United States Patent
Baym et al.

(10) Patent No.: US 9,232,896 B2
(45) Date of Patent: *Jan. 12, 2016

(54) FOCUSING ELECTROMAGNETIC RADIATION WITHIN A TURBID MEDIUM USING ULTRASONIC MODULATION

(71) Applicant: Elwha LLC, Bellevue, WA (US)

(72) Inventors: Michael H. Baym, Cambridge, MA (US); Roderick A. Hyde, Redmond, WA (US); Jordin T. Kare, Seattle, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 580 days.

This patent is subject to a terminal disclaimer.

(21) Appl. No.: 13/623,681

(22) Filed: Sep. 20, 2012

(65) Prior Publication Data

US 2014/0081102 A1    Mar. 20, 2014

(51) Int. Cl.
*A61B 5/05* (2006.01)
*A61B 5/00* (2006.01)
*G02F 1/33* (2006.01)
*A61B 5/1455* (2006.01)

(52) U.S. Cl.
CPC .......... *A61B 5/0097* (2013.01); *G02F 1/33* (2013.01); *A61B 5/0086* (2013.01); *A61B 5/14551* (2013.01); *A61B 5/4064* (2013.01)

(58) Field of Classification Search
USPC .......................................................... 600/407
See application file for complete search history.

(56) References Cited

U.S. PATENT DOCUMENTS

| | | | |
|---|---|---|---|
| 4,329,876 A | 5/1982 | Chen et al. | |
| 5,174,298 A | 12/1992 | Dolfi et al. | |
| 5,212,667 A | 5/1993 | Tomlinson, Jr. et al. | |
| 5,293,873 A | 3/1994 | Fang | |
| 5,738,101 A * | 4/1998 | Sappey | 600/476 |
| 5,751,243 A | 5/1998 | Turpin | |
| 5,951,481 A | 9/1999 | Evans | |
| 6,002,958 A | 12/1999 | Godik | |
| 6,041,248 A | 3/2000 | Wang | |
| 6,176,829 B1 | 1/2001 | Vilkomerson | |
| 6,424,857 B1 | 7/2002 | Henrichs et al. | |
| 6,738,653 B1 | 5/2004 | Sfez et al. | |

(Continued)

OTHER PUBLICATIONS

PCT International Search Report; International App. No. PCT/US13/60402; Dec. 9, 2013; pp. 1-2.

(Continued)

*Primary Examiner* — Joel F Brutus

(57) ABSTRACT

The present disclosure provides various systems and methods for focusing electromagnetic radiation (EMR) within a diffusion medium, such as a turbid medium. A diffusion medium is irradiated with EMR. The EMR may be modulated by an acoustical wave focused on a focus volume within the diffusion medium. The EMR may be modulated by a beat frequency or other function of multiple focused acoustical waves. The EMR may be modulated at a harmonic of a fundamental frequency of one or more acoustical waves. A filter may filter the emerging EMR to remove all but specifically modulated EMR scattered from the focus volume. The modulated EMR may be focused and/or used for various purposes, including imaging. In some embodiments, the modulated EMR may be reflected and/or amplified by a phase conjugating mirror. Furthermore, in some embodiments, acoustical phase conjugation may be used to focus an acoustical wave on a focus volume.

43 Claims, 19 Drawing Sheets

(56) References Cited

U.S. PATENT DOCUMENTS

| | | | |
|---|---|---|---|
| 6,815,694 B2 | 11/2004 | Sfez et al. | |
| 7,144,370 B2 | 12/2006 | Fomitchov et al. | |
| 7,319,639 B2 | 1/2008 | Heyman | |
| 7,541,602 B2 | 6/2009 | Metzger et al. | |
| 7,623,285 B2 | 11/2009 | Gross et al. | |
| 2002/0057757 A1* | 5/2002 | Khoury | 378/21 |
| 2004/0099815 A1 | 5/2004 | Sfez et al. | |
| 2004/0127782 A1* | 7/2004 | Sfez et al. | 600/407 |
| 2005/0107694 A1 | 5/2005 | Jansen et al. | |
| 2005/0163186 A1 | 7/2005 | Petersen | |
| 2005/0256403 A1 | 11/2005 | Fomitchov et al. | |
| 2006/0058685 A1 | 3/2006 | Fomitchov et al. | |
| 2006/0122475 A1 | 6/2006 | Balberg et al. | |
| 2006/0247506 A1 | 11/2006 | Balberg et al. | |
| 2007/0002327 A1 | 1/2007 | Zhou et al. | |
| 2007/0151343 A1 | 7/2007 | Gross et al. | |
| 2008/0033297 A1* | 2/2008 | Sliwa | 600/439 |
| 2008/0177180 A1* | 7/2008 | Azhari et al. | 600/439 |
| 2008/0296514 A1 | 12/2008 | Metzger et al. | |
| 2008/0312533 A1 | 12/2008 | Balberg et al. | |
| 2009/0264722 A1 | 10/2009 | Metzger et al. | |
| 2010/0000330 A1 | 1/2010 | Rokni et al. | |
| 2010/0076352 A1 | 3/2010 | Kim et al. | |
| 2010/0168577 A1 | 7/2010 | Vezina | |
| 2011/0071402 A1* | 3/2011 | Masumura | 600/476 |
| 2012/0182561 A1 | 7/2012 | Masumura | |
| 2012/0184830 A1 | 7/2012 | Balberg et al. | |

OTHER PUBLICATIONS

PCT International Search Report; International App. No. PCT/US13/60408; Dec. 9, 2013; pp. 1-2.

Elson et al.; "Ultrasound-mediated optical tomography: a review of current methods"; Interface Focus; published online Jun. 2, 2011; pp. 632-648; vol. 1; The Royal Society; located at http://rsfs.royalsocietypublishing.org.

Kemp et al.; "Security applications of terahertz technology"; Terahertz for Military and Security Applications; 2003; bearing a date of Feb. 5, 2015; pp. 44-52; vol. 5070; SPIE; located at: http://proceedings.spiedigitallibrary.org.

Kotilahti et al.; "Near-Infrared Spectroscopic Imaging"; Wiley Encyclopedia of Biomedical Engineering; 2006; printed on May 17, 2015; pp. 1-12; John Wiley & Sons, Inc.

Miyamoto et al.; "Fabrication of multilayered photochromic memory media using pressure-sensitive adhesives"; Applied Optics; Nov. 20, 2006; pp. 8424-8427; vol. 45, No. 33; Optical Society of America.

Tan et al.; "Interfacial properties and in vitro cytotoxic effects of surface-modified near infrared absorbing Au-Au2S nanoparticles"; J Mater Sci: Mater Med; published online May 26, 2009; pp. 2091-2103; vol. 20; Springer Science+Business Media, LLC.

Wang et al; "Frequency-swept ultrasound-modulated optical tomography of scattering media"; Optics Letters; Jun. 15, 1998; pp. 975-977; vol. 23, No. 12; Optical Society of America.

Wang, Lihong V.; "Ultrasonic Modulation of Scattered Light in Turbid Media and a Potential Novel Tomography in Biomedicine"; Photochemistry and Photobiology; 1998; bearing a date of Apr. 15, 1997; pp. 41-49; vol. 67, No. 1; American Society for Photobiology (As provided by Examiner).

Yaqoob et al; Optical Phase Conjugation for Turbidity Suppression in Biological Samples ; Nature Photonics; 2008; bearing a date of Jun. 1, 2009; pp. 1-16, vol. 2, No. 2; NIH Public Access Author Manuscript.

Mahan, Engler et al., "Ultrasonic Tagging of Light: Theory", PNAS, v95, p. 14015 (1998).

Wang et al., "Ultrasound-modulated optical tomography of absorbing object buried in dense tissue-simulating turbid media", Applied Optics, v36, p. 7277 (1997).

Xu et al., "Time-reversed Ultrasonically Encoded Optical Focusing into Scattering Media", Nature Photonics, Online Publication, Jan. 16, 2011.

* cited by examiner

FOCUSING ELECTROMAGNETIC RADIATION WITHIN A TURBID MEDIUM USING ULTRASONIC MODULATION

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

NONE

RELATED APPLICATIONS

U.S. patent application Ser. No. 13/623,703, entitled FOCUSING ELECTROMAGNETIC RADIATION WITHIN A TURBID MEDIUM USING ULTRASONIC MODULATION, naming Michael H. Baym, Roderick A. Hyde, Jordin T. Kare, and Lowell L. Wood, Jr. as inventors, filed 20 Sep. 2012, is related to the present application.

U.S. patent application Ser. No. 13/623,717, entitled FOCUSING ELECTROMAGNETIC RADIATION WITHIN A TURBID MEDIUM USING ULTRASONIC MODULATION, naming Michael H. Baym, Roderick A. Hyde, Jordin T. Kare, and Lowell L. Wood, Jr. as inventors, filed 20 Sep. 2012, is related to the present application.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

TECHNICAL FIELD

This disclosure relates to modulating electromagnetic radiation (EMR) scattered within a diffusion medium, such as a turbid medium, using ultrasonic vibrations to modulate the EMR. Additionally, this disclosure relates to phase conjugation of EMR and/or acoustical waves.

SUMMARY

In various instances it may be useful to focus electromagnetic radiation (EMR) within a diffusion medium, such as a turbid medium that scatters the EMR. Various systems and methods for focusing EMR within a diffusion medium are provided herein. In some embodiments, a focus volume within a diffusion medium is vibrated using an ultrasonic acoustical wave. The diffusion medium is irradiated with EMR and the EMR that scatters from the focus volume is modulated (i.e., shifted or tagged) by a function of the frequency of the acoustical wave. A detector or receiver may then receive the modulated EMR from the focus volume. In some embodiments, EMR modulated by a harmonic of the frequency of the acoustical wave may be detected.

In some embodiments, the received modulated EMR may be reflected and/or amplified back into the diffusion medium using a phase conjugating mirror. The reflected EMR may follow a turbid path through the diffusion medium to arrive at the focus volume. The phase conjugated EMR may be received and/or detected after re-emerging from the diffusion medium. In some embodiments, the modulated EMR and/or the phase conjugated EMR may be used to image the focus volume, activate a drug within the focus volume, provide a therapeutic service, measure a flow rate, measure an absorption rate, and/or otherwise be used.

Acoustical waves focused on the focus volume may be diffused within the diffusion medium. In some embodiments, acoustical waves scattered from the focus volume within the diffusion medium may be reflected and/or amplified using an acoustical phase conjugating mirror. The phase conjugated acoustical waves may improve focus and/or the intensity of vibration with a focus volume. EMR scattered from the focus volume may be filtered and/or phase conjugated.

In some embodiments, multiple acoustical waves may be used to modulate the EMR within the focus volume at a function of the frequency of a first acoustical wave and a second acoustical wave. In some embodiments, the EMR scattered from the focus volume may be detected and/or filtered that is at a beat frequency of two or more acoustical waves.

In some embodiments, EMR may be spectroscopically encoded along a scan line by vibrating a plurality of focus volumes within a diffusion medium each at a different acoustical frequency. In some embodiments, the received modulated EMR may then be used to determine the location along the scan line from which it was received. The received modulated EMR may be filtered, reflected, and/or amplified using a phase conjugating mirror.

In some embodiments, EMR may be focused on an interface between layers of a layered diffusion medium. For example, a region of a layer, such as a surface between two layers, may be vibrated using an ultrasonic acoustical wave. EMR scattered from the vibrated region may be modulated by the vibrations. The modulated EMR from the region may be received, filtered, and/or otherwise utilized. For example, an image of the interface between layers may be generated using the filtered modulated EMR from the surface between two layers. In some embodiments, a layer of the diffusion medium may include printed text on a surface that may be imaged using the systems and methods described herein.

DETAILED DESCRIPTION

Figure 1:
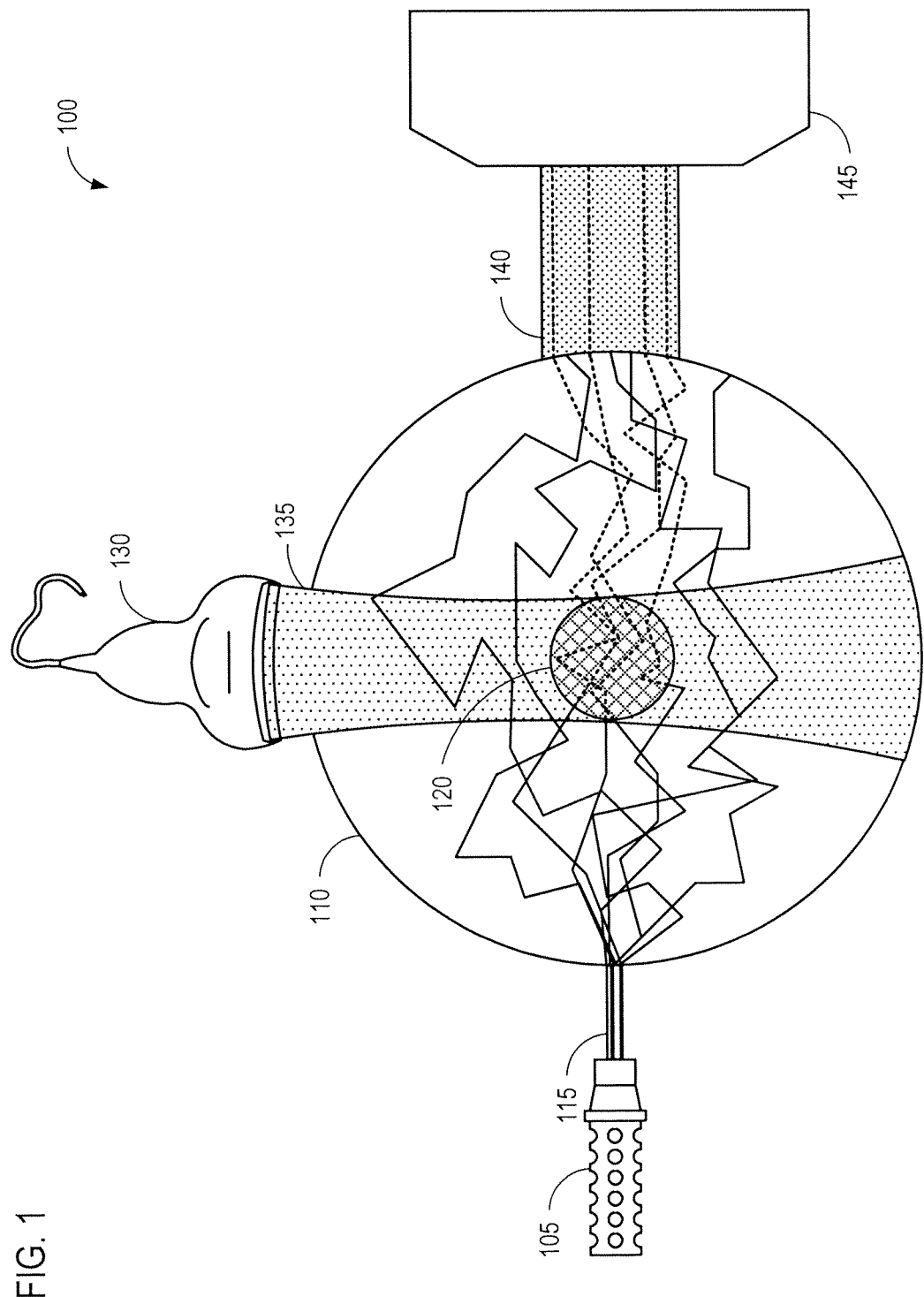
FIG. 1 illustrates electromagnetic radiation (EMR) irradiating a focus volume vibrated using a focused acoustical wave within a diffusion medium.

In various situations, it may be desirable to probe, image, and/or otherwise interact with diffusion media, such as turbid media, in a non-invasive manner. Electromagnetic radiation (EMR), such as infrared light, may be able to penetrate the diffusion medium. However, due to the turbidity of the diffusion medium, it may not be adequately focused within the diffusion medium to generate images, provide light therapy, and/or otherwise interact with a focus region within the diffusion medium.

According to various embodiments, a focus volume within a diffusion medium may be vibrated using a focused acoustical wave. For example, one or more ultrasonic transducers may be used to focus an acoustical wave on a focus volume within a turbid medium. The one or more acoustical waves may vibrate the focus volume at an intensity or frequency detectably greater and/or different than other portions of the diffusion medium. The diffusion medium may be irradiated with EMR. For example, a laser may be used to irradiate the diffusion medium with EMR having a relative narrow bandwidth.

The EMR may experience random scattering due to the turbidity of the diffusion medium. A receiver may receive the diffused EMR scattered from the diffusion medium, including modulated EMR frequency shifted by a function of the frequency(ies) of the one or more acoustical waves. A filter may be used to remove EMR at the original, unmodulated frequency. The filtered modulated EMR may be representative of EMR scattered from the focus volume. The filtered modulated EMR may be used, for example, to image the focus volume within the diffusion medium.

In some embodiments, the filtered modulated EMR may be reflected by a phase conjugating mirror back into the focus volume. A phase conjugating mirror may reflect the filtered modulated EMR and return it back through the diffusion medium to the focus volume. The phase conjugated EMR may travel the same turbid path through the diffusion medium to arrive at the focus volume. However, a high percentage of the phase conjugated EMR will arrive at the focus volume since the phase conjugated EMR will traverse its original path in reverse.

EMR scattered from the focus volume may be shifted (upward or downward) by the frequency of an acoustical wave. In addition, some of the EMR scattered from the focus volume may be shifted by a harmonic of the frequency of an acoustical wave. The intensity of the EMR shifted by a harmonic of the frequency of the acoustical wave may be greatest where the intensity of the acoustical wave is greatest. Accordingly, the harmonically modulated EMR from the focus volume may represent EMR scattered from the focus volume. The signal-to-noise ratio of the harmonically modulated EMR scattered from the focus volume (as opposed to other locations within the diffusion medium) may be higher for the second harmonic of the acoustical wave than the fundamental frequency of the acoustical wave. Increased signal-to-noise ratios and/or tighter focuses may be obtained using the second, third, fourth, . . . , Nth harmonics in place of or in addition to the fundamental frequency of the acoustical wave. The received EMR scattered by the focus volume may be filtered to exclude all but the EMR modulated at any one or more harmonic of the fundamental frequency of an acoustical wave.

An acoustical wave focused on the focus volume may be scattered by the turbid medium. Receiving acoustical waves scattered from the focus volume and reflecting them back to the focus volume using acoustical phase conjugation may allow for a higher intensity acoustical wave within the focus volume and/or a tighter focus volume.

As previously described, any number of acoustical waves may be used to vibrate the focus volume within the diffusion medium. For example, two acoustical waves—a first acoustical wave and a second acoustical wave—may be used to vibrate the focus volume. In various embodiments, one or both of the first and second acoustical waves may be a focused acoustical wave focused on the focus volume. EMR scattered from the focus volume may be frequency shifted by a function of the frequency of the first acoustical wave and the frequency of the second acoustical wave; the frequency shift from either wave may be upwards or downwards in frequency. In some embodiments, a receiver may receive, potentially in conjunction with a filter, EMR scattered from the focus volume shifted by a difference of the frequencies of the first and second acoustical waves, shifted by a sum of the frequencies of the first and second acoustical waves, shifted by a beat frequency of the first and second acoustical waves, and/or shifted by another function of the first and second acoustical waves.

In some embodiments, the focus volume may include a continuous plurality of focus volumes along a scan line within a diffusion medium. Each of the focus volumes may be vibrated at a unique acoustical frequency, beginning at a first frequency at a first end of the scan line and ending at a second frequency at a second end of the scan line. In some embodiments, the plurality of focus volumes may be a continuous elongated focus volume vibrated at a first frequency at a first end of the elongated focus volume and transitioning to a second frequency at a second end of the scan line using a plurality of frequencies of acoustical waves. In some embodiments, acoustical diffraction may be used to obtain a plurality of unique frequencies along the scan line by diffracting one or more acoustical waves.

In some embodiments, one or more acoustical waves may be pulsed, chirped, frequency modulated, amplitude modulated, and/or phase modulated. Acoustical modulation may allow for time-stamps to be associated with received modulated EMR. Using velocity of EMR and/or acoustical waves within the diffusion medium and the time stamps associated with the EMR may allow for imaging of specific regions or focus volumes of the diffusion medium.

In conjunction with any of the embodiments described herein, the EMR scattered from the focus volume and/or the phase conjugated EMR scattered from the focus volume may be analyzed to determine the absorption rate of the EMR in hemoglobin within the focus volume in order to calculate a blood oxygenation within the focus volume. Similarly, the received EMR and/or the received phase conjugated EMR may be used to determine neuronal activity within a brain, such as via the use of continuous wave functional near-infrared (fNIR) imaging spectroscopy, frequency domain fNIR imaging spectroscopy, time-resolved fNIR imaging spectroscopy, and/or other spectroscopic analysis of diffusion mediums.

Additionally, the received EMR and/or the received phase conjugated EMR may be used to determine a characteristic of a motion of a fluid within a focus volume. The received EMR and/or the received phase conjugated EMR may be used to generate an image of the focus volume and/or activate a drug within the focus volume. In some embodiments, the phase conjugated EMR may be amplified relative to the amplitude of the filtered modulated EMR, such as by using a laser amplifier or using a pumping beam to create an energy build-up in a non linear standing wave in a phase conjugating mirror.

In any of the embodiments described herein, the frequency of one or more acoustical waves may be between 200 kilohertz and 100 megahertz. An acoustical wave may be generated using a transducer, such as a piezoelectric transducer, a magnetostrictive transducer, a mechanical transducer, and/or an opto-acoustical transducer. The focused acoustical wave used in conjunction with any of the various embodiments described herein may comprise a high-intensity focused ultrasonic wave. An acoustical wave may be focused using an acoustical lens, a phased array of ultrasonic transducers, and/or a curved surface of an ultrasonic transducer. In various embodiments, e.g., to improve the frequency discrimination of acoustically encoded EMR, the frequency bandwidth of the EMR used may be less than that of the acoustical frequency. In embodiments involving a plurality of focus volumes vibrated at different acoustical frequencies, the frequency bandwidth of the EMR used may be less than the difference in acoustical frequencies used to vibrate nearby focus volumes.

The EMR may be generated using any of a wide variety of EMR sources, including a laser, a superluminescent diode, an ultrashort pulsed laser, and/or a supercontinuum laser. The frequency bandwidth of the EMR may include frequencies between 600 nanometers and 1000 nanometers, ultraviolet frequencies, visible light frequencies, infrared frequencies, and/or other frequencies useful for imaging, providing an EMR therapy, detection, analysis, and/or another function. The EMR may be swept from an initial frequency to a final frequency. The EMR may be pulsed, amplitude modulated, frequency modulated, and/or continuously emitted.

EMR scattered from the focus volume and received by a receiver may be filtered as described herein. The filtered EMR may be phase conjugated using a phase conjugating mirror back to the focus volume. The phase conjugating mirror may utilize four-wave mixing and/or any of a wide variety of electrical, electro-optical, and/or mechanical phase conjugating mirrors. The phase conjugated EMR transmitted back to the focus volume may be amplified, phase shifted, and/or frequency shifted prior to entering the diffusion medium. For example, an acousto-optical modulator, an electro-optical modulator, and/or another modulation device may be used to modify the phase conjugated EMR.

The diffusion medium may comprise any of a wide variety of turbid mediums, including human tissue, organic tissue, inorganic tissue, inorganic compounds, layered diffusion mediums, volumetric optical memory, and/or other turbid mediums. In some embodiments, an acoustical wave may be focused on an interface or surface between two layers of a diffusion medium. EMR scattered from the focus region may be used to generate an image of a surface of an embedded layer. In some embodiments, the surface of the layer may contain printed text. In such embodiments, the text and/or the EMR may be selected such that the material forming the layers is transparent to the EMR while the text is opaque.

Some of the infrastructure that can be used with embodiments disclosed herein is already available, such as general-purpose computers, computer programming tools and techniques, digital storage media, and communication networks. A computing device may include a processor such as a microprocessor, a microcontroller, logic circuitry, or the like. The processor may include a special purpose processing device such as application-specific integrated circuits (ASIC), programmable array logic (PAL), programmable logic array (PLA), a programmable logic device (PLD), field programmable gate array (FPGA), or another customizable and/or programmable device. The computing device may also include a machine-readable storage device such as non-volatile memory, static RAM, dynamic RAM, ROM, CD-ROM, disk, tape, magnetic, optical, flash memory, or other machine-readable storage medium. Various aspects of certain embodiments may be implemented using hardware, software, firmware, or a combination thereof.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor do the steps need to be executed only once.

FIG. 1 illustrates a system 100 for focusing EMR within a diffusion medium. As illustrated, a light source 105 is used to irradiate a diffusion medium 110 with EMR 115. The EMR 115 scatters within the diffusion medium 110. At least a portion of the EMR 140 may exit the diffusion medium 110 and be received by a receiver 145. A transducer 130 may be configured to generate an ultrasonic acoustical wave 135. The transducer 130 may be configured to focus the ultrasonic acoustical wave 135 on a focus volume 120 within the diffusion medium 110.

The light source 105 may irradiate the diffusion medium 110 with EMR 115 at a frequency or frequency bandwidth, $f_r$. The EMR 115 scattered from the focus volume 120, where the intensity of the ultrasonic acoustical wave 135 is greatest, may be modulated by the frequency, $f_a$, of the ultrasonic acoustical wave 135. That is, the frequency of the EMR 115 scattered from the focus volume 120 may be shifted by $\pm f_a$. Accordingly, EMR 140 emerging from the diffusion medium may include modulated EMR. The receiver 145 may be configured to receive the modulated EMR. In some embodiments, a filter (not shown in FIG. 1) may be configured to filter out the EMR at the original frequency, $f_r$, leaving only the modulated EMR scattered from the focus volume 120.

The modulated EMR scattered from the focus volume 120 may be used to generate an image of the focus volume 120, detect a blood oxygenation within the focus volume 120, determine a fluid flow within the focus volume 120, provide an EMR therapy to the focus volume 120, burn the focus volume 120, activate a drug within the focus volume 120, determine neuronal activity within a focus volume 120 in a brain, and/or provide another function as described herein.

The dimensions and relative sizes of the diffusion medium, the focus volume, the scattered EMR, and the focused acoustical wave may not be to scale in the figures and are intended for illustrative purposes only. Additionally, in the illustrated embodiments, the EMR is shown as entering one side of a diffusion medium and being received on another side of the diffusion medium. In practice, the EMR may irradiate the diffusion medium from one or more locations and from one or more angles. It will be appreciated that the EMR may scatter from the diffusion medium, including from the focus volume and exit the diffusion medium at any location. Accordingly, a detector, receiver, and/or filter may be configured to detect, receive, and/or filter EMR emitted from any of the surfaces of the diffusion medium. For example, a receiver may substantially surround the diffusion medium in order to receive EMR emitted from any location.

Figure 2:
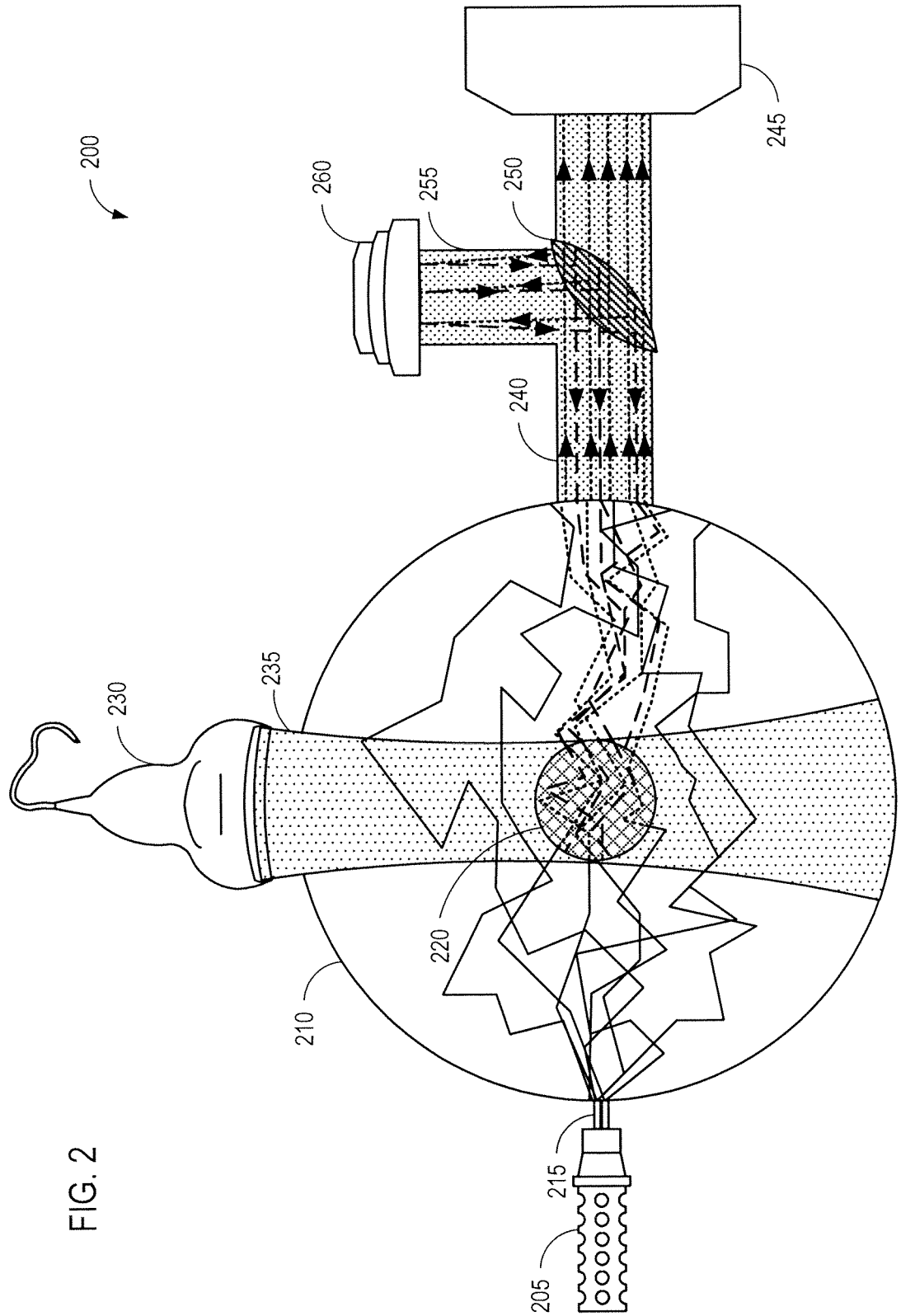
FIG. 2 illustrates EMR scattered by the focus volume modulated at the acoustical frequency and received via a phase conjugating mirror.

FIG. 2 illustrates system 200 configured to focus EMR on a focus volume 220 within a diffusion medium 210 using a phase conjugating mirror 260. As illustrated, a light source 205 may irradiate the diffusion medium 210 with EMR 215. The EMR 215 may scatter within the diffusion medium 210. An ultrasonic transducer 230 may generate an ultrasonic acoustical wave 235 focused on the focus volume 220. EMR 215 scattered from the focus volume 220 may be modulated by the frequency, $f_a$, of the ultrasonic acoustical wave 235.

EMR 240 emerging from the diffusion medium 210 may include EMR at an original radiation frequency, $f_r$, and at a modulation frequency $f_r \pm N f_a$, where N is a non-zero integer. The EMR at the radiation frequency, $f_r$, may be filtered. In some embodiments, the modulated EMR at a frequency(ies), $f_r \pm N f_a$, may be received by a receiver 245. A beam splitter 250 may be used to direct some or all of the modulated EMR emerging from the diffusion medium 210 to a phase conjugating mirror 260. Phase conjugated EMR 255 may then be directed back into the diffusion medium 210. The phase conjugated EMR 255 may follow the same turbid path in the reverse direction back to the focus volume 220 and again emerge from the diffusion medium 210. The phase conjugated EMR 255 scattered from the focus volume 220 may then be received by the receiver 245.

Again, the relative locations of the light source 205, the phase conjugating mirror 260, the beam splitter 250, and the receiver 245 are for illustrative purposes only. For example, the phase conjugated EMR 255 scattered from the focus volume 220 may emerge from the diffusion medium 210 from substantially the same location the original EMR 215 entered the diffusion medium 210. Accordingly, it may be useful to have a receiver(s), light source(s), phase conjugating mirror(s), and/or other system components that substantially envelope the diffusion medium 210, substantially envelope a portion of the diffusion medium 210, and/or are strategically located relative to locations where EMR is anticipated to enter and/or emerge from the diffusion medium 210.

Because the phase conjugated EMR 255 comprises phase conjugated EMR generated from EMR 240 scattered and frequency shifted from the focus volume 220, the phase conjugated EMR 255 emerging from the diffusion medium 210 can be assumed to have been scattered substantially from the focus volume 220. By receiving the phase conjugated EMR 255 emerging from the diffusion medium 210 after being scattered from the focus volume 220, any number of analyses may be performed.

For example, the received phase conjugated EMR 255 may be used to calculate a blood oxygenation within the focus volume 220, determine neuronal activity within a portion (the focus volume 220) of a brain (the diffusion medium 210), a characteristic of a motion of a fluid within the focus volume 220, generate an image of the focus volume 220, active a drug within the focus volume 220, provide EMR therapy to the focus volume 220, burn the focus volume 220, and/or provide another function. According to various embodiments, using the EMR known to have been scattered from the focus volume, a system may utilize continuous wave fNIR imaging spectroscopy, frequency domain fNIR imaging spectroscopy, time-resolved fNIR imaging spectroscopy, and/or other spectroscopic analysis that would otherwise be unusable due to the turbid nature of the diffusion medium 210.

Figure 3:
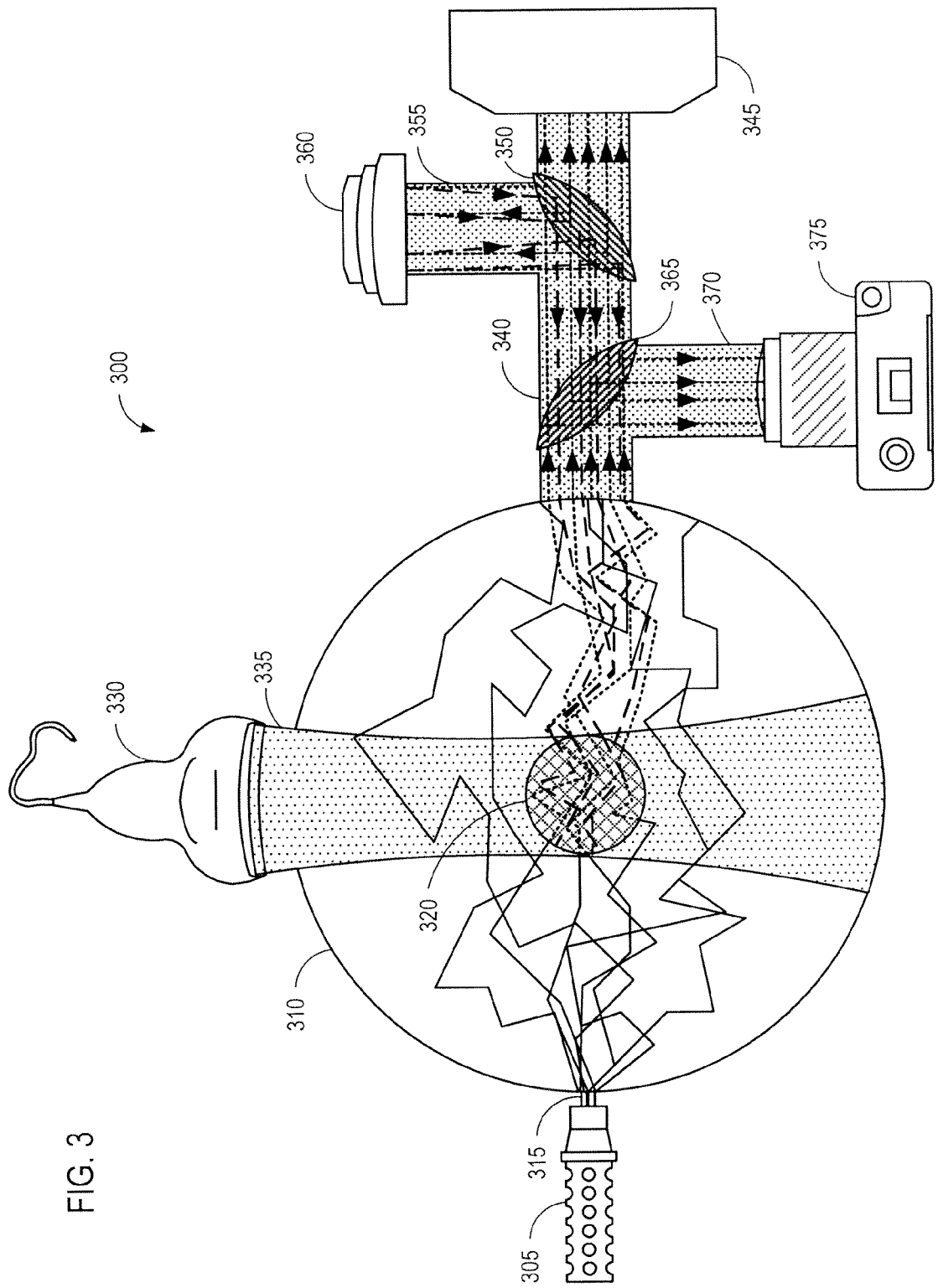
FIG. 3 illustrates an imaging device configured to receive modulated light scattered from the vibrating focus volume.

FIG. 3 illustrates an example of a system 300 in which an imaging device 375 is configured to generate an image of the focus volume 320 using modulated EMR 340 and/or phase conjugated EMR 355 scattered from the focus volume 320. In the illustrated embodiment, a light source 305 may irradiate the focus volume 320 within the diffusion medium 310. An ultrasonic transducer 330 may generate an ultrasonic acoustical wave 335 focused on the focus volume 320. EMR 315 scattered from the focus volume 320 may be modulated by the frequency, $f_a$, of the acoustical wave.

EMR 340 emerging from the diffusion medium may include EMR at an original radiation frequency, $f_r$, and at a modulation frequency $f_r \pm Nf_a$, where N is a non-zero integer. The EMR at the radiation frequency, $f_r$, may be removed via a filter. In some embodiments, the modulated EMR 340 at a frequency(ies), $f_r \pm Nf_a$, may be received by a receiver 345. A beam splitter 350 may be used to direct some or all of the modulated EMR 340 emerging from the diffusion medium 310 to a phase conjugating mirror 360. Phase conjugated EMR 355 may then be directed back into the diffusion medium 310. The phase conjugated EMR 355 may follow the same turbid path in the reverse direction back to the focus volume 320 and again emerge from the diffusion medium 310. The phase conjugated EMR 355 scattered from the focus volume 320 may then be received by the receiver 345.

In addition, a beam splitter 365 may be configured to direct some (or all at a selective time interval(s)) of the modulated EMR 340 and/or the phase conjugated EMR 370 scattered from the focus volume 320 to the imaging device 375. The system 300 may use the imaging device 375 to generate an image of the focus volume 320.

In some embodiments, the beam splitter 350 and/or the receiver 345 may be omitted. In such an embodiment, EMR 315 may enter the diffusion medium 310 and be scattered. Some of the EMR 315 may be scattered by or within the focus volume 320. The portion of the EMR 315 scattered by the focus volume 320 may be modulated by $\pm Nf_a$. The modulated EMR 340 emerging from the diffusion medium 310 may be separated, filtered, and/or otherwise distinguished from the EMR 340 emerging from the diffusion medium 310 at the original radiation frequency, $f_r$. A portion of the modulated EMR 340 may be directed toward the imaging device 375. A portion of the modulated EMR 340 may be directed toward the phase conjugating mirror 360.

The phase conjugated EMR 355 generated by phase conjugating mirror 360 may be amplified, intensified, phase shifted, frequency shifted, modulated, and/or otherwise manipulated and transmitted via a reverse turbid path through the diffusion medium 310 back to the focus volume 320. The phase conjugated EMR 355 may be scattered by the focus volume 320 and ultimately received, at least in part, by the imaging device 375. The imaging device 375 may be configured to generate an image of the focus volume 320 using the modulated EMR 340 and/or the phase conjugated EMR 355 scattered by the focus volume 320. Again, the illustrated locations of the various components of the system 300 are merely exemplary, as are the paths of the EMR inside and outside of the diffusion medium 310.

Figure 4:
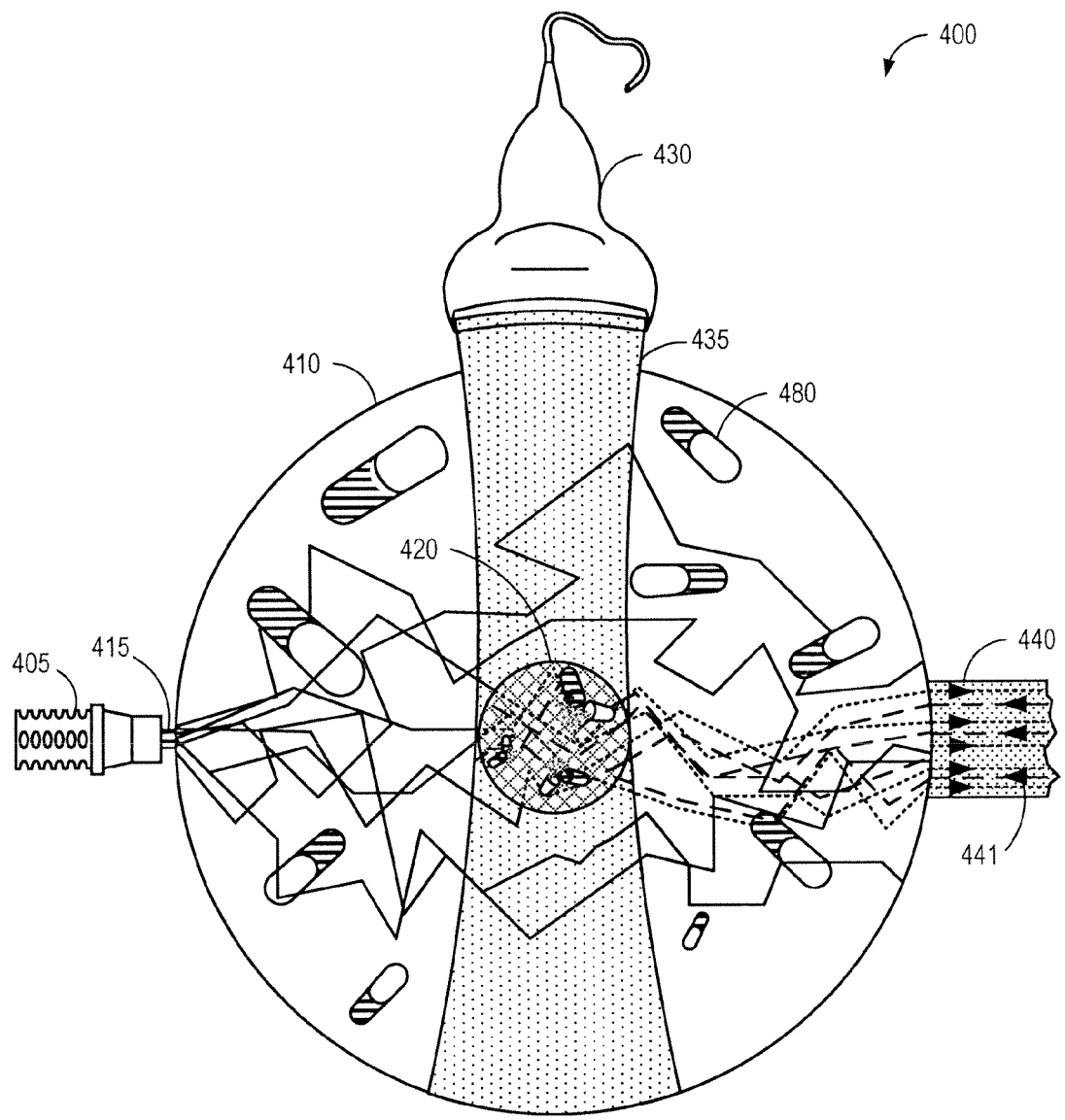
FIG. 4 illustrates a drug distributed throughout a diffusion medium and activated only within a focus volume using a phase conjugating mirror to reflect modulated EMR.

FIG. 4 illustrates a system 400 in which amplified phase conjugated EMR 440 is used to selectively activate drugs 480 within a focus volume 420 of a diffusion medium 410. As illustrated, a light source 405, such as a laser, may be used to irradiate a diffusion medium 410. A medication or other drug 480 may be distributed throughout the diffusion medium 410 in an inactive state. The drug 480 may be configured to be selectively activated by EMR of a particular frequency and/or intensity.

The EMR 415 output by the light source 405 may be configured to not activate the drug 480 within the diffusion medium 410. The EMR 415 may scatter within the diffusion medium 410. A transducer 430 may generate a focused ultrasonic acoustical wave 435 focused on the focus volume 420 within the diffusion medium 410. The EMR 415 that scatters from the focus volume 420 may be modulated by a function of the frequency of the ultrasonic acoustical wave 435. The EMR 440, including EMR modulated at the function of the frequency of the ultrasonic acoustical wave 435, may emerge from the diffusion medium 410.

Not illustrated in FIG. 4, in some embodiments a filter may be used to filter out the EMR at the originally emitted frequency. The modulated EMR 440 that emerges from the diffusion medium 410 may be reflected by a phase conjugating mirror. The phase conjugated EMR 441 may traverse the turbid path through the diffusion medium 410 back to the focus volume 420. In some embodiments, the phase conjugated EMR 441 may be amplified by a laser and/or by a standing wave within the phase conjugating mirror. In such embodiments, the intensity of the phase conjugating EMR 441 that is scattered from the focus volume 420 may be sufficient to selectively activate the drug 480 within the focus volume 420, while not activating the drug 480 outside of the focus volume 420. Alternatively or additionally, the frequency of the phase conjugated EMR 441 may be adjusted to a frequency adapted to activate the drug 480 within the focus volume 420, while not activating the drug 480 outside of the focus volume 420.

Figure 5:
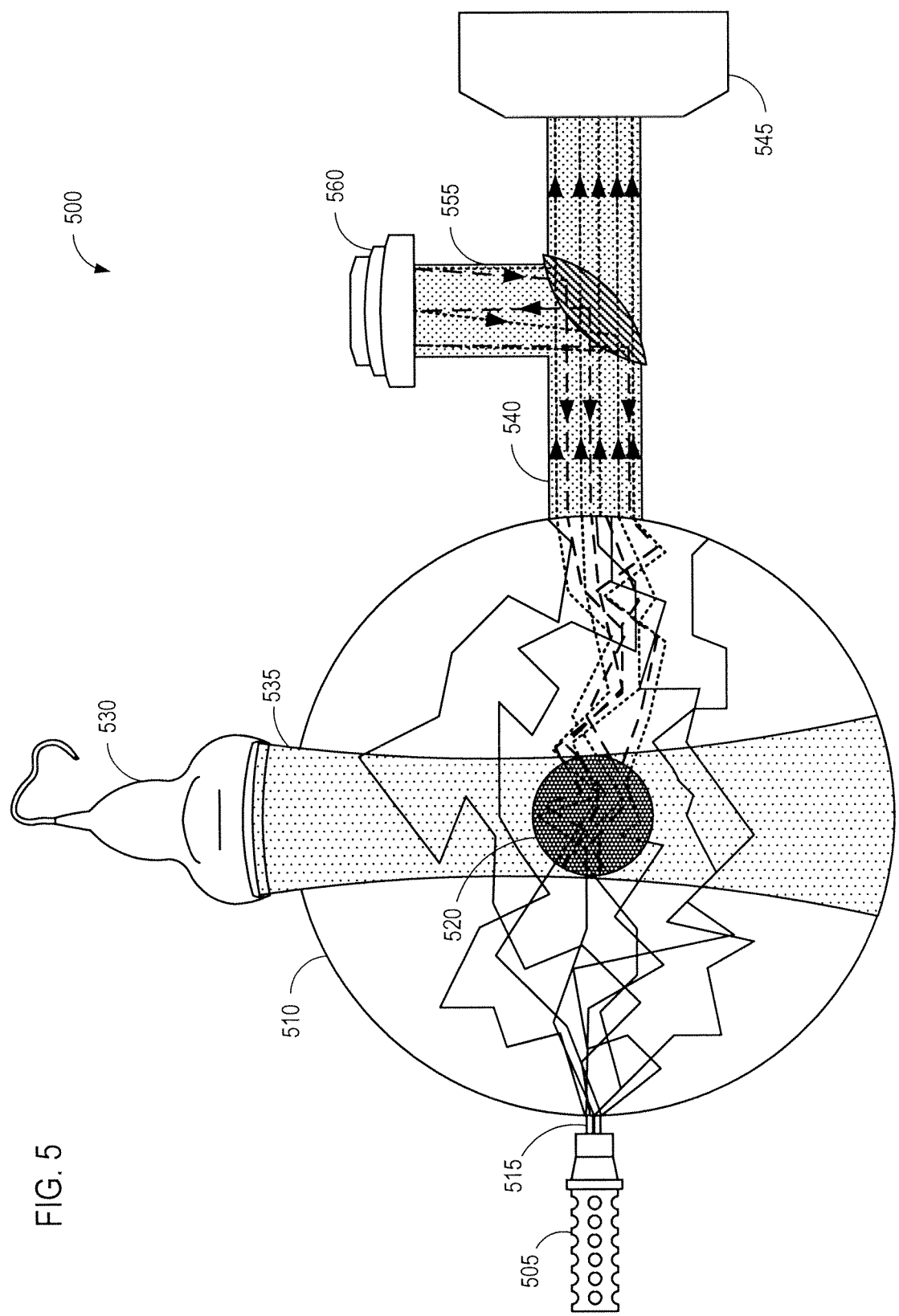
FIG. 5 illustrates a focus volume within a diffusion medium being intensely radiated with EMR using a phase conjugating mirror to reflect modulated EMR.

FIG. 5 illustrates a system 500 in which phase conjugation of modulated EMR is used to provide an EMR therapy to a focus volume 520 within a diffusion medium 510. As illustrated, a light source 505, such as a laser, may be used to irradiate a diffusion medium 510. The EMR 515 output by the light source 505 may not have a sufficient intensity or include a correct frequency bandwidth to provide a predetermined EMR therapy treatment. The EMR 515 may scatter within the diffusion medium 510. A transducer 530 may generate a focused ultrasonic acoustical wave 535 focused on the focus volume 520 within the diffusion medium 510. The EMR 515 that scatters from the focus volume 520 may be modulated by a function of the frequency of the ultrasonic acoustical wave 535. The EMR 540, including EMR modulated at the function of the frequency of the ultrasonic acoustical wave 535, may emerge from the diffusion medium 510.

In some embodiments, a filter may be used to filter out the EMR at the originally emitted frequency, leaving only EMR scattered from the focus volume 520 and modulated by the ultrasonic acoustical wave 535. The modulated EMR 540 that emerges from the diffusion medium 510 may be received by a receiver 545 and/or by a phase conjugating mirror 560. The phase conjugated EMR 555 may traverse the turbid path through the diffusion medium 510 back to the focus volume 520. In some embodiments, the phase conjugated EMR 555 may be amplified by a laser and/or by a standing wave within the phase conjugating mirror 560. In such embodiments, the intensity of the phase conjugated EMR 555 that returns to the focus volume 520 may be sufficient to provide a desired EMR therapy within the focus volume 520, while not providing the EMR therapy within the rest of the diffusion medium 510. Alternatively or additionally, the frequency of the phase conjugated EMR 555 may be adjusted to a frequency suitable for EMR therapy within the focus volume 520, while not providing the EMR therapy within the rest of the diffusion medium 510.

Figure 6:
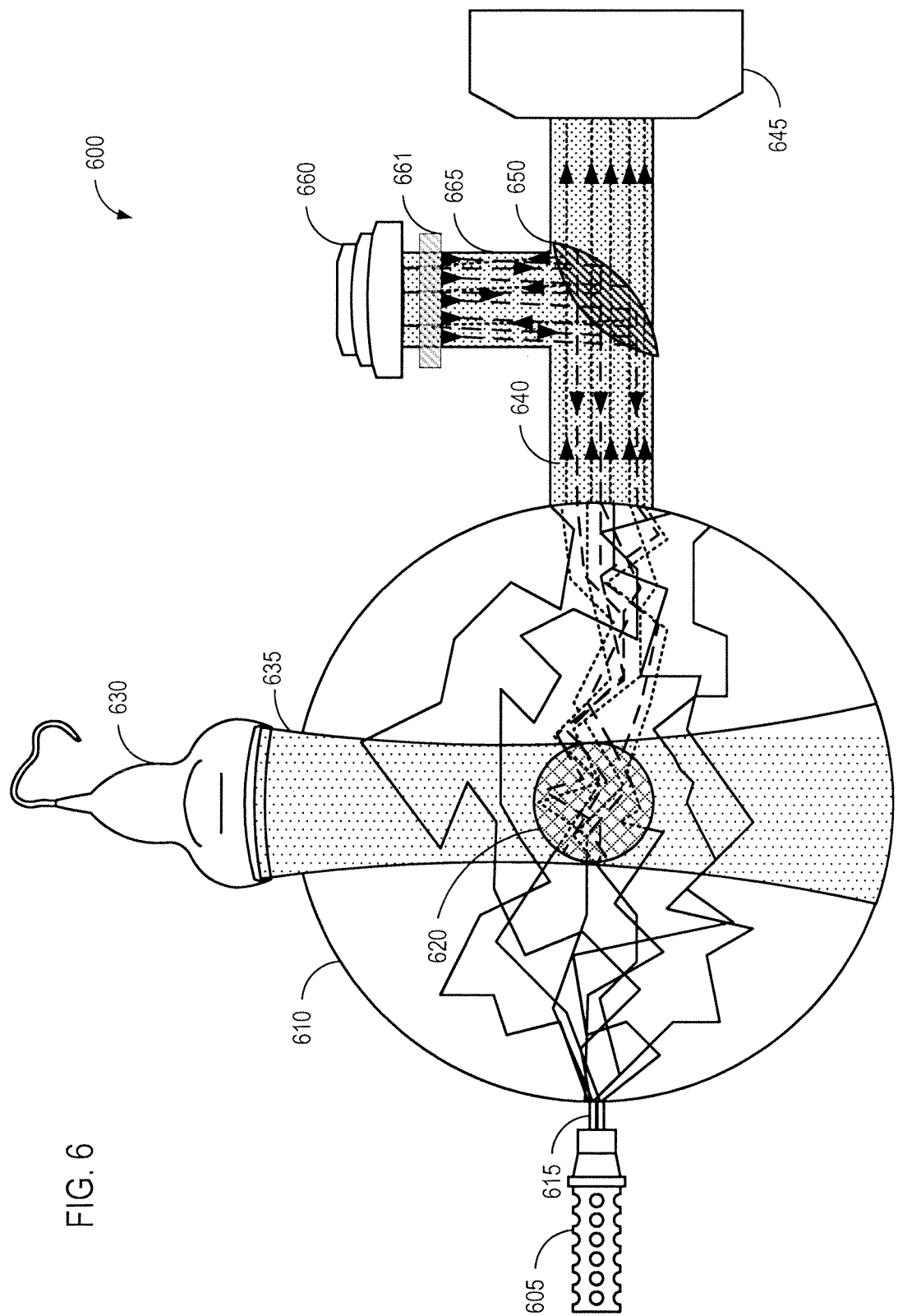
FIG. 6 illustrates the usage of an in-line photo multiplier used in conjunction with a phase conjugating mirror in an acoustically encoded optical focusing system.

FIG. 6 illustrates a system 600 in which phase conjugated EMR 665 is amplified using a photo-multiplying device 661, such as a laser amplification system. Similar to previous embodiments, a light source 605, such as a laser, may be used to irradiate a diffusion medium 610. The EMR 615 may scatter within the diffusion medium 610. A transducer 630 may generate a focused ultrasonic acoustical wave 635 focused on the focus volume 620 within the diffusion medium 610. The EMR 615 that scatters from the focus volume 620 may be modulated by a function of the frequency of the ultrasonic acoustical wave 635. The EMR 640, including EMR modulated at the function of the frequency of the ultrasonic acoustical wave 635, may emerge from the diffusion medium 610.

In some embodiments, a filter may be used to filter out the EMR at the originally emitted frequency, leaving only EMR scattered from the focus volume 620 and modulated by the ultrasonic acoustical wave 635. The modulated EMR 640 that emerges from the diffusion medium 610 may be split by a beam splitter 650 and received by a receiver 645 and/or by a phase conjugating mirror 660. The phase conjugated EMR 665 may be amplified using the photo-multiplying device 661. The amplified phase conjugated EMR 665 may traverse the turbid path through the diffusion medium 610 back to the focus volume 620.

Figure 7:
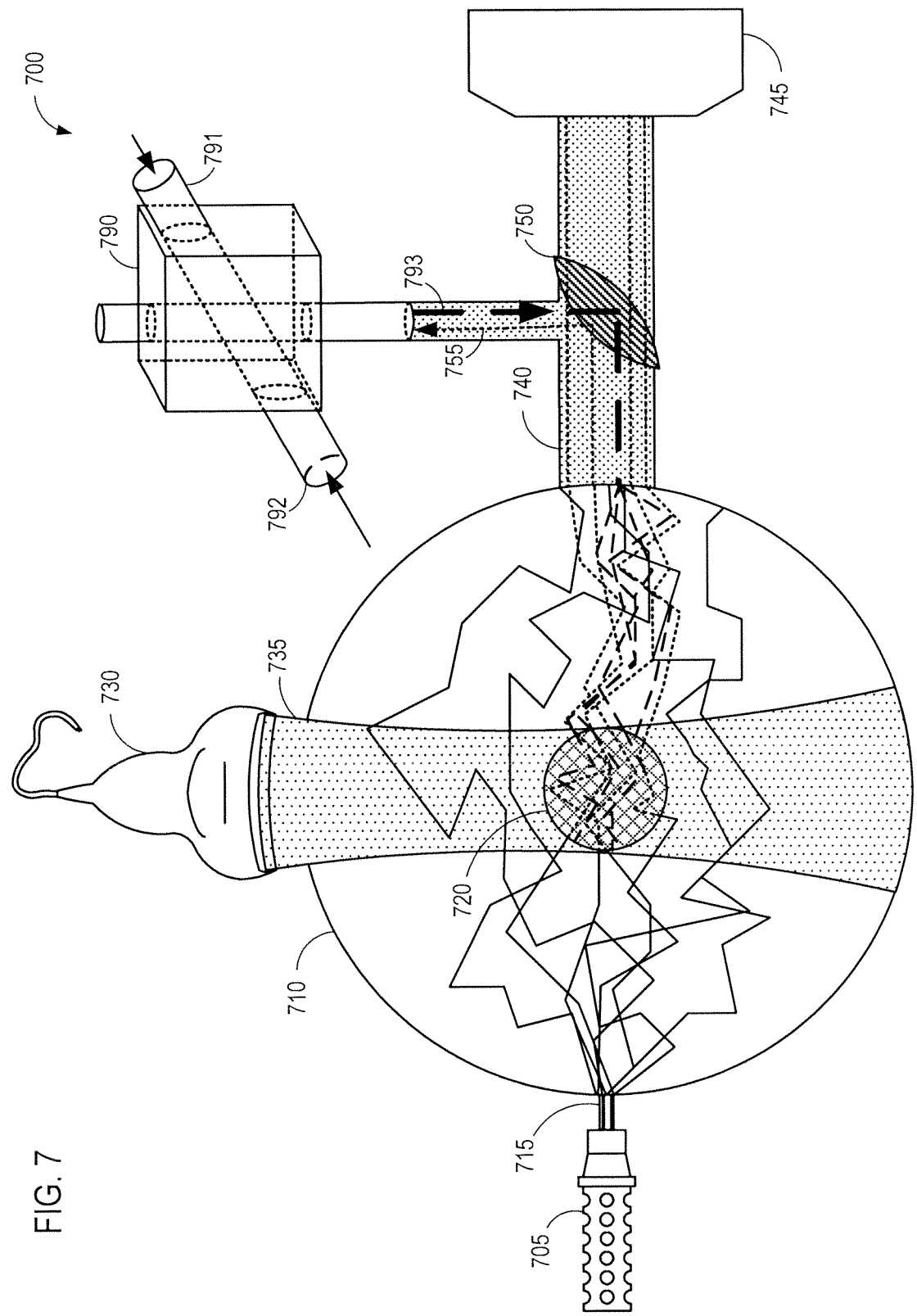
FIG. 7 illustrates an embodiment of a phase conjugating mirror including pumping beams to generate an amplified reflection of the acoustically encoded EMR.

FIG. 7 illustrates a system 700 in which phase conjugated EMR 793 is amplified by pumping beams in a phase conjugating mirror that create an amplifying standing wave. Again, a light source 705 may be used to irradiate a diffusion medium 710. The EMR 715 may scatter within the diffusion medium 710. A transducer 730 may generate a focused ultrasonic acoustical wave 735 focused on the focus volume 720 within the diffusion medium 710. The EMR 715 that scatters from the focus volume 720 may be modulated by a function of the frequency of the ultrasonic acoustical wave 735. The EMR 740, including EMR modulated at the function of the frequency of the ultrasonic acoustical wave 735, may emerge from the diffusion medium 710.

In some embodiments, a filter may be used to filter out the EMR at the originally emitted frequency, leaving only EMR scattered from the focus volume 720 and modulated by the ultrasonic acoustical wave 735. The modulated EMR 740 that emerges from the diffusion medium 710 may be split by a beam splitter 750 and received by a receiver 745 and/or by a phase conjugating mirror 790. The phase conjugating mirror 790 may include two pumping beams 791 and 792 adapted to amplify the phase conjugated EMR 793 directed toward the focus volume 720. The amplified phase conjugated EMR 793 may traverse the turbid path through the diffusion medium 710 back to the focus volume 720.

Figures 8, 9:
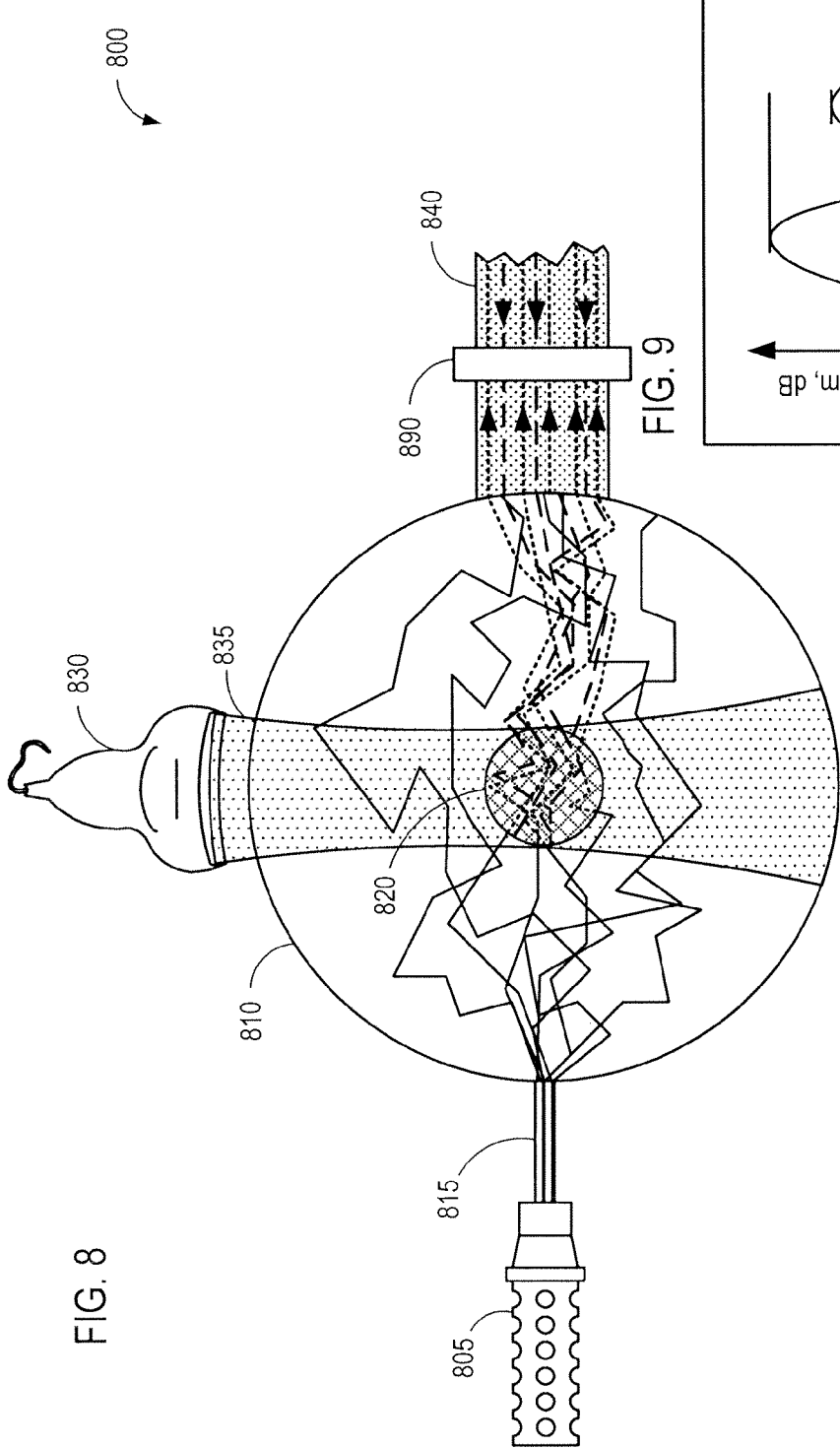
FIG. 8 illustrates an embodiment of an acoustically encoded optical focusing system configured to utilize EMR modulated at an Nth harmonic of the acoustical wave.
FIG. 9 illustrates an exemplary graphical illustration of the power spectrum of the fundamental frequency and a second harmonic of an acoustical wave.

FIG. 8 illustrates a system 800 in which EMR 840 modulated at an Nth harmonic of a fundamental frequency of an acoustical wave 835 is detected. As illustrated, a light source 805 may be used to irradiate a diffusion medium 810. The EMR 815 may scatter within the diffusion medium 810. A transducer 830 may generate a focused ultrasonic acoustical wave 835 focused on a focus volume 820 within the diffusion medium 810. The focused ultrasonic acoustical wave 835 may cause the diffusion medium 810, and particularly the focus volume 820, to vibrate at a fundamental frequency of the ultrasonic acoustical wave 835. Where the intensity of the ultrasonic acoustical wave 835 is greatest (i.e., the focus volume 820), the focus volume 820 may also vibrate at appreciable levels at various harmonics of the fundamental frequency.

The EMR 815 scattered by the focus volume 820 may be modulated by a function of the fundamental frequency of the acoustical wave 835. When detecting the modulated EMR 815 scattered by the focus volume 820, there may be some "noise" generated by the modulated EMR 815 scattered by the diffusion medium 810. Some EMR 815 scattered by the focus volume 820 may be modulated at an Nth harmonic of the fundamental frequency of the ultrasonic acoustical wave 835. The signal-to-noise ratio of the EMR 815 scatted by the focus volume 820 at an Nth harmonic of the fundamental frequency of the acoustical wave 835 may be greater than the signal-to-noise ratio of the EMR 815 scattered by the focus volume 820 at the fundamental frequency of the acoustical wave 835.

Accordingly, a filter 890 may be configured to filter the EMR emerging from the diffusion medium 810 to remove the EMR at the original radiation frequency and the EMR modulated at the fundamental frequency. In some embodiments, the filter 890 may be configured to remove EMR modulated at any number of harmonics. For example, it may be desirable to filter all but the EMR modulated at a third harmonic of the fundamental frequency of the acoustical wave 835.

The harmonically modulated EMR 840 that emerges from the diffusion medium 810 may ultimately be split by a beam splitter, received by a receiver, and/or reflected by a phase conjugating mirror, as described herein in accordance with other embodiments.

FIG. 9 illustrates an exemplary power spectrum in decibels of an acoustical wave with a local maximum at a fundamental harmonic and a local maximum at a second harmonic. Any harmonic may be used in conjunction with the presently described systems and methods.

Figure 10:
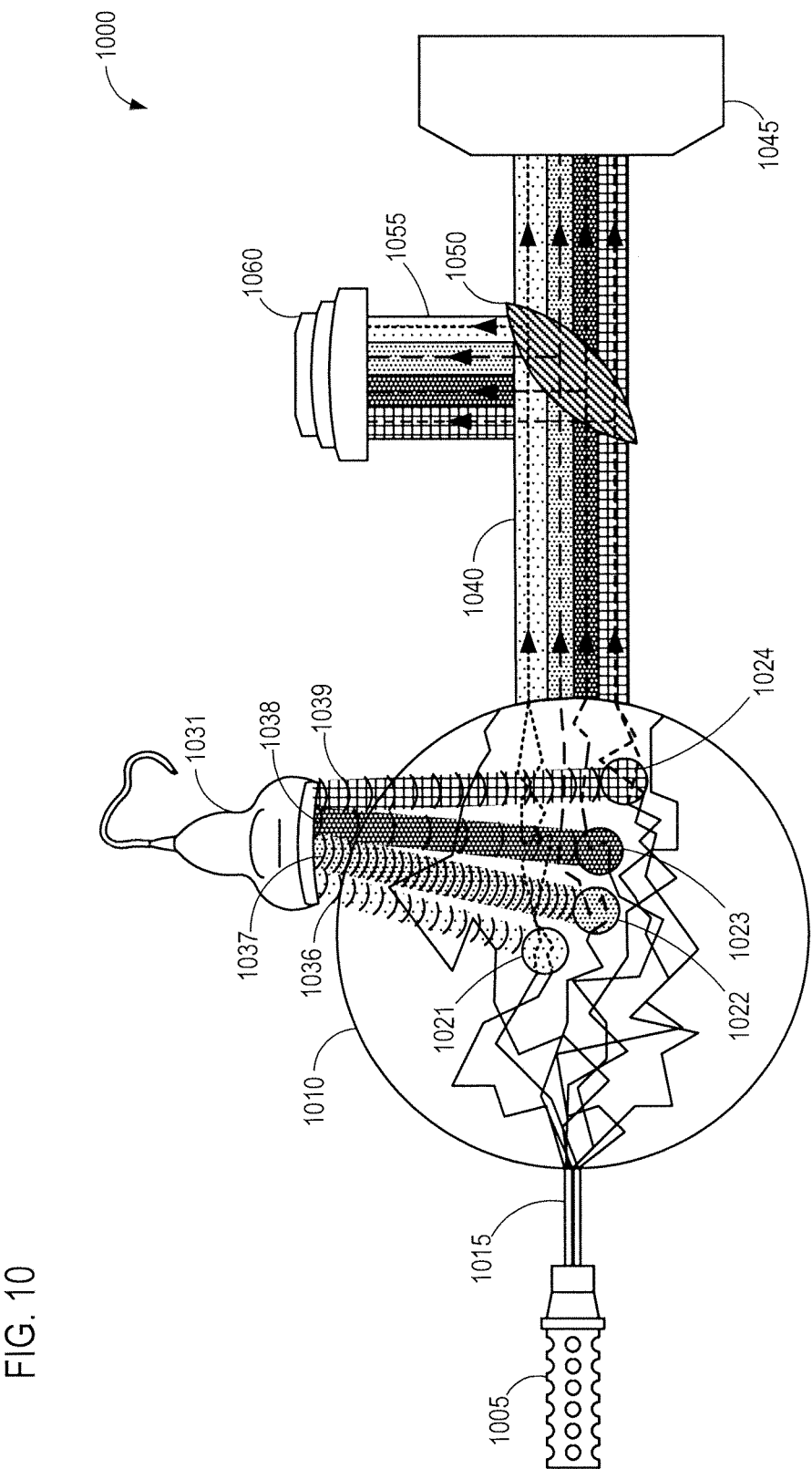
FIG. 10 illustrates multiple focus volumes within a diffusion medium, each vibrating at a different frequency using a focused acoustical wave.

FIG. 10 illustrates a system 1000 in which multiple focus volumes 1021, 1022, 1023, and 1024 are used to modulate EMR 1015. A light source 1005 may be used to irradiate a diffusion medium 1010. The EMR 1015 may scatter within the diffusion medium 1010. A transducer 1031 may generate multiple focused ultrasonic acoustical waves 1036, 1037, 1038, and 1039 focused on the focus volumes 1021, 1022, 1023, and 1024 within the diffusion medium 1010. The EMR 1015 that scatters from the focus volumes 1021, 1022, 1023, and 1024 may be modulated by a function of the frequency of the ultrasonic acoustical waves 1036, 1037, 1038, and 1039, respectively. The EMR 1040, including EMR modulated at the function of the various frequencies of the ultrasonic acoustical waves 1036, 1037, 1038, and 1039, respectively, may emerge from the diffusion medium 1010.

The modulated EMR 1040 that emerges from the diffusion medium 1010 may be split by a beam splitter 1050, received by a receiver 1045, and/or reflected by a phase conjugating mirror 1060. Phase conjugated EMR 1055 may be reflected back to traverse the turbid path through the diffusion medium 1010 back to the respective focus volumes 1021, 1022, 1023, and 1024. In some embodiments, an imaging device may be used to image each of the respective focus volumes 1021, 1022, 1023, and 1024 based on the uniquely modulated EMR scattered from each focus volume.

In some embodiments, the transducer 1031 may be configured to generate a single acoustical wave that is then acoustically diffracted to generate each unique focused acoustical wave 1036, 1037, 1038, and 1039. Alternatively, the transducer 1031 may be configured to generate a single acoustical wave that is then acoustically diffracted to generate a continuum of focused acoustical waves beginning at a first acoustical frequency and ending at a second acoustical frequency, wherein focused acoustical waves 1036, 1037, 1038, and 1039 are included in the continuum of focused acoustical waves.

Figure 11A:
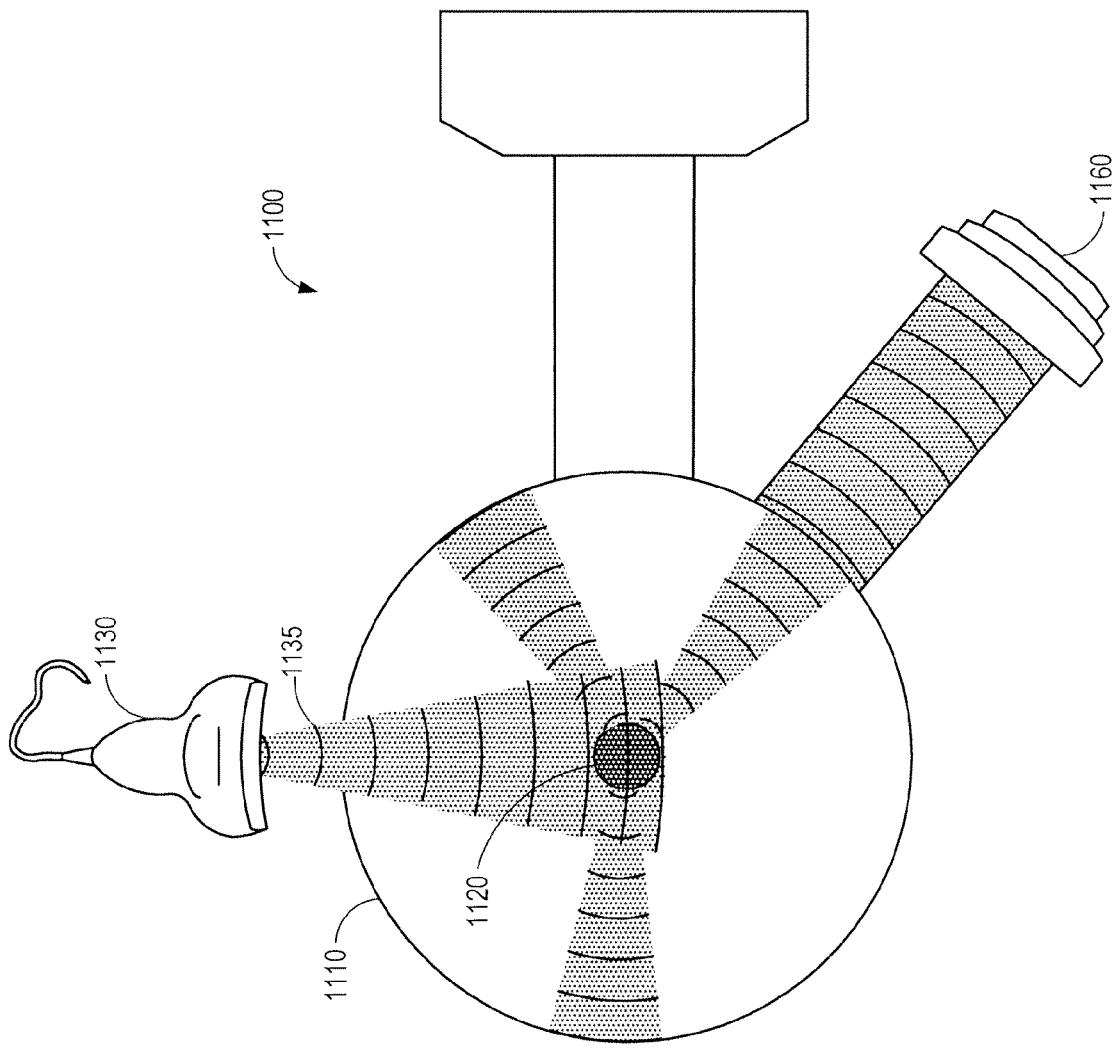
FIG. 11A illustrates a focused acoustical wave scattered from a focus volume within a diffusion medium.

FIG. 11A illustrates a system 1100 in which a focused acoustical wave 1135 is scattered from a focus volume 1120 within a diffusion medium 1110. As illustrated, the system 1100 may include a transducer 1130 configured to generate the focused acoustical wave 1135. The focused acoustical wave 1135 may be at least partially diffused within diffusion medium 1110. At least some of the focused acoustical wave 1135 may be scattered from the focus volume 1120 and emerge from the diffusion medium 1110. Some or all of the focused acoustical wave 1135 scattered from the focus volume 1120 and emerging from the diffusion medium 1110 may be received by an acoustical phase conjugating mirror 1160.

Figure 11B:
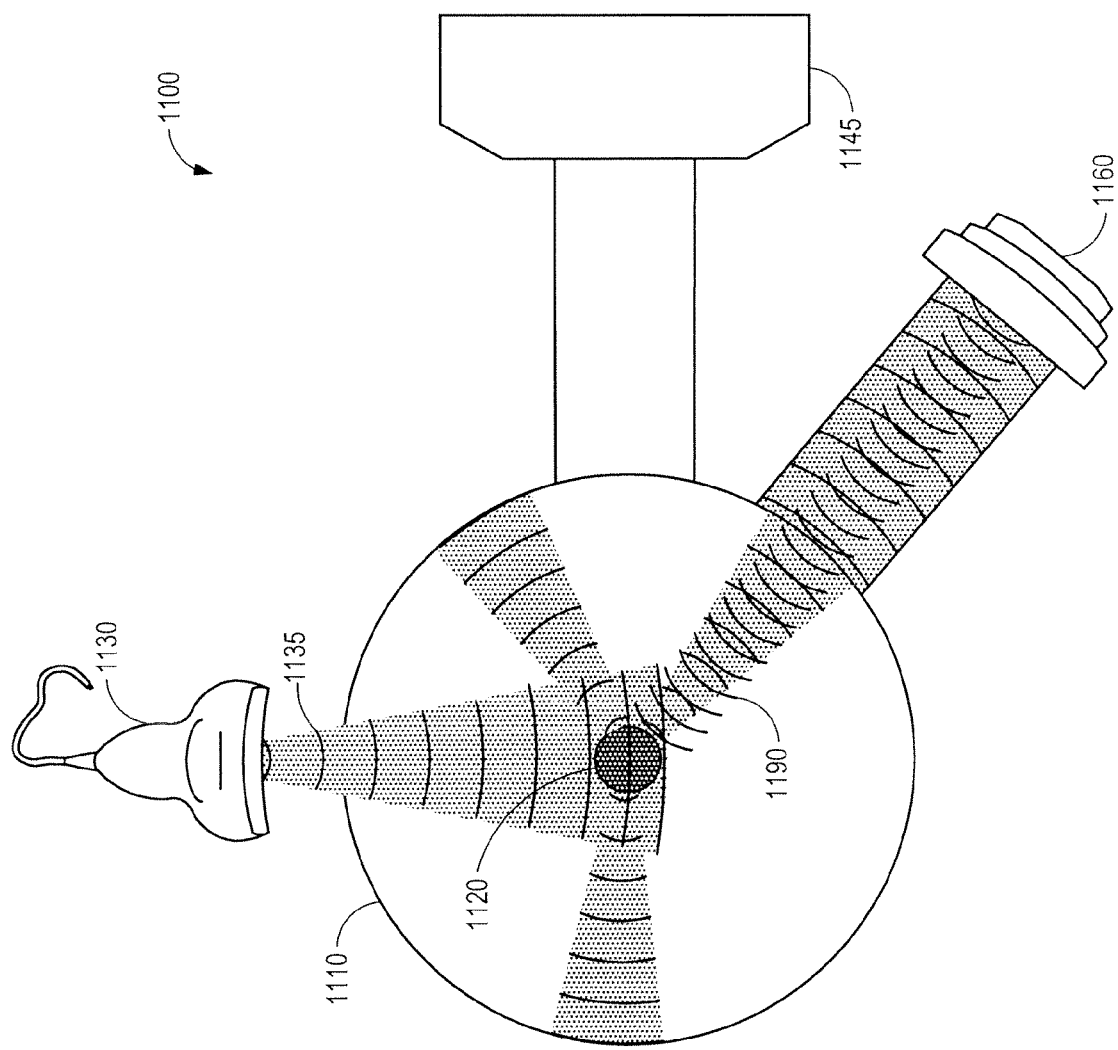
FIG. 11B illustrates an acoustical wave scattered from the focus volume being reflected by an acoustical phase conjugating mirror back to the focus volume.

As illustrated in FIG. 11B, phase conjugating mirror 1160 may reflect a phase conjugated acoustical wave 1190 to the focus volume 1120. The phase conjugated acoustical wave 1190 may be amplified. The phase conjugated acoustical wave 1190 may increase the intensity with which the focus volume is vibrated, thereby increasing the signal-to-noise ratio of EMR scattered from the focus volume 1120 and detected by receiver 1145.

Acoustical phase conjugation may be performed using any of a wide variety of systems and methods for acoustical phase conjugation. The phase conjugation of ultrasonic acoustical waves may be performed by the transformation of a wave field resulting in the reversal of the propagation of the waves while conserving the initial spatial distribution of amplitudes and phases. In one embodiment, a microprocessor may be used to control a matrix of piezoelectric transducers configured to transmit a phase conjugated acoustical wave of a received acoustical wave. Alternatively, multichannel parametric systems utilizing reflecting surfaces oscillating at a double-frequency of the incoming ultrasonic wave may be utilized. In some embodiments, acoustical phase conjugation may be performed in a crystal by alternating an electromagnetic field to control a sound velocity within the crystal. In other embodiments acoustical and/or optical phase conjugation may be performed by leveraging the phonon-plasmon interaction in semiconductors by alternating an electric field or by a modulated optical pump. Additionally, parametric ultrasonic phase conjugation in magnetic ceramics may be used to produce a, potentially amplified, phase conjugated ultrasonic acoustical wave.

Figure 12A:
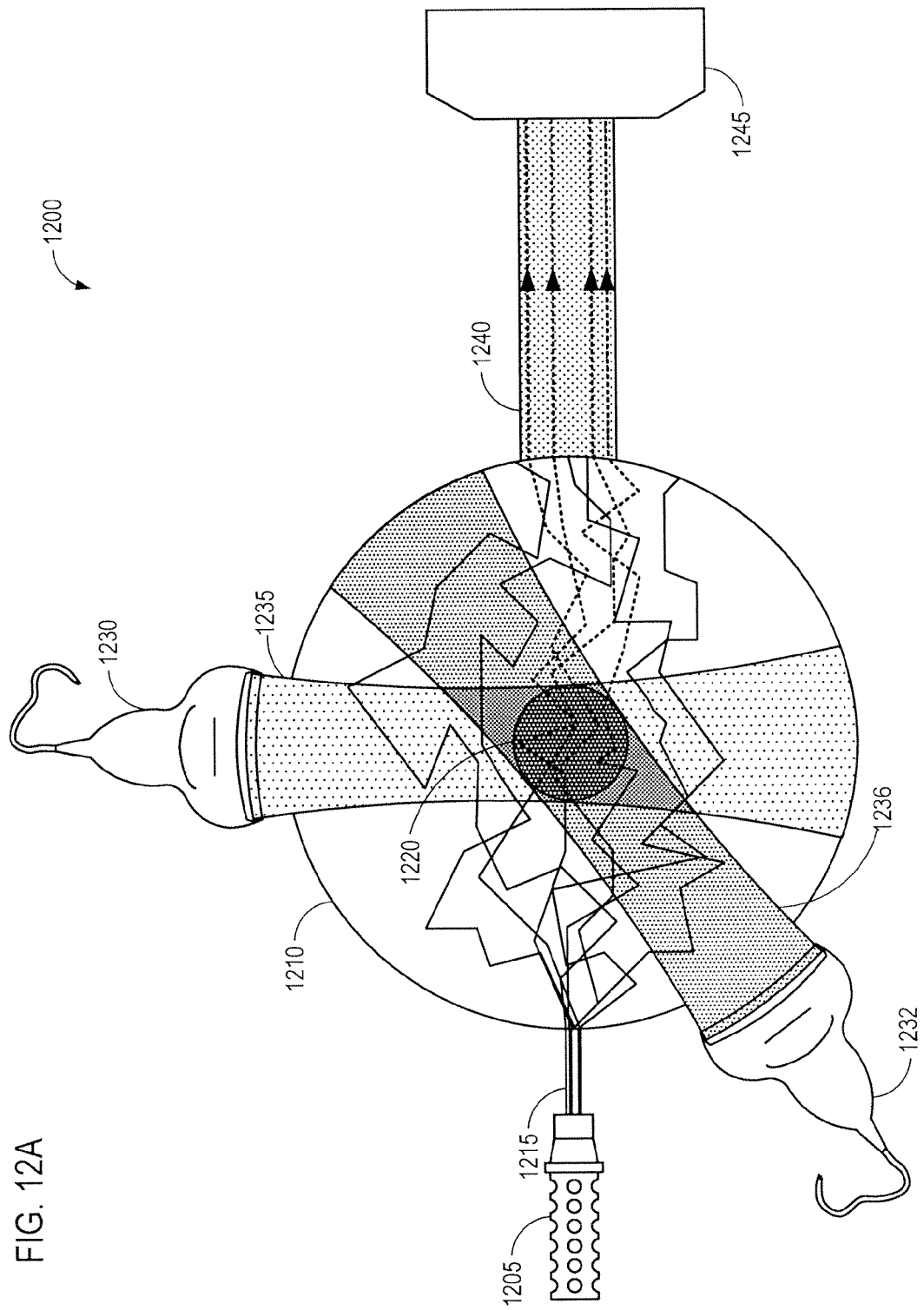
FIG. 12A illustrates two focused acoustical waves used to modulate EMR within a focus volume of a diffusion medium.

FIG. 12A illustrates a system 1200 in which two focused ultrasonic acoustical waves 1235 and 1236 are used to modulate EMR 1215 within a focus volume 1220 of a diffusion medium 1210. As illustrated, a light source 1205 may be used to irradiate a diffusion medium 1210. The EMR 1215 may scatter within the diffusion medium 1210. A first transducer 1230 may generate a first focused ultrasonic acoustical wave 1235 focused on the focus volume 1220 within the diffusion medium 1210. The first focused ultrasonic acoustical wave 1235 may cause the diffusion medium 1210, and particularly the focus volume 1220, to vibrate at a fundamental frequency of the first acoustical wave 1235. A second transducer 1232 may generate a second focused ultrasonic acoustical wave 1236 focused on the focus volume 1220 within the diffusion medium 1210.

At the focus volume 1220, where the first and second ultrasonic acoustical waves 1235 and 1236 intersect, the diffusion medium 1210 may vibrate at the fundamental frequency of the first acoustical wave 1235, the fundamental frequency of the second acoustical wave 1236, any harmonic of the fundamental frequencies of the first and second acoustical waves 1235 and 1236, and any function of the respective frequencies of the first and second acoustical waves 1235 and 1236, including harmonics thereof and associated beat frequencies.

In one embodiment, some of the EMR 1215 scattered by the focus volume 1220 may be modulated by a beat frequency of the first acoustical wave 1235 and the second acoustical wave 1236. A receiver 1245 may be configured to detect, receive, and/or otherwise utilize EMR 1240 modulated by the beat frequency of the first and second acoustical waves 1235 and 1236. In some embodiments, a filter may be configured to remove EMR scattered from the diffusion medium 1210 that is not modulated at the beat frequency.

Figure 12B:
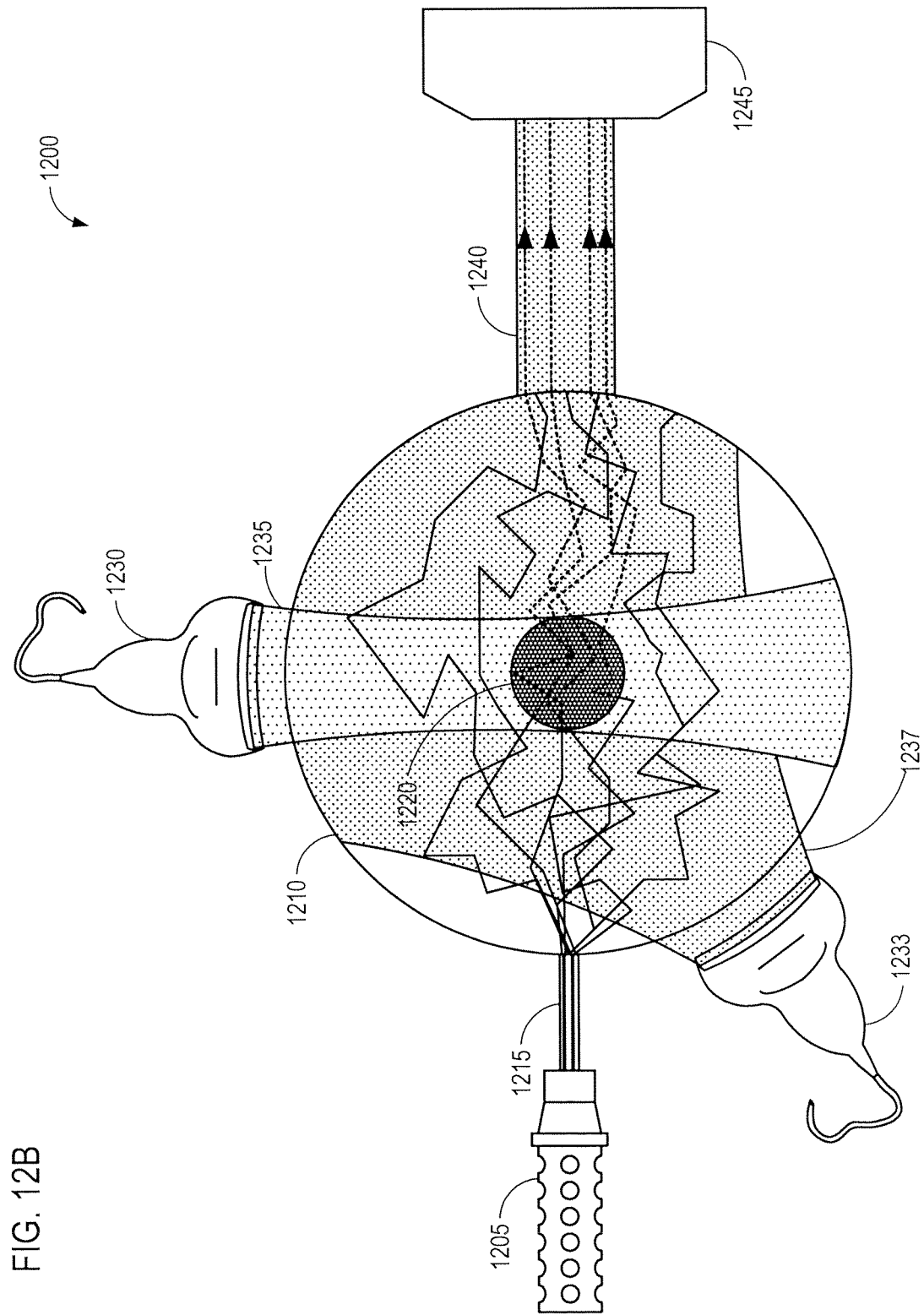
FIG. 12B illustrates a first acoustical wave and a second, focused acoustical wave modulating EMR within a focus volume of a diffusion medium.

FIG. 12B illustrates an alternative embodiment, in which a second transducer 1233 generates an unfocused ultrasonic acoustical wave 1237 that is generally diffused within the diffusion medium 1210. In such an embodiment, all or most of the EMR 1215 scattered from the diffusion medium 1210 may be modulated by a function of the frequency of the second acoustical wave 1237. The EMR 1215 scattered from the focus volume 1220 may be modulated by a function of the frequencies, such as a beat frequency, of the first and second acoustical waves 1235 and 1237.

Figure 12C:
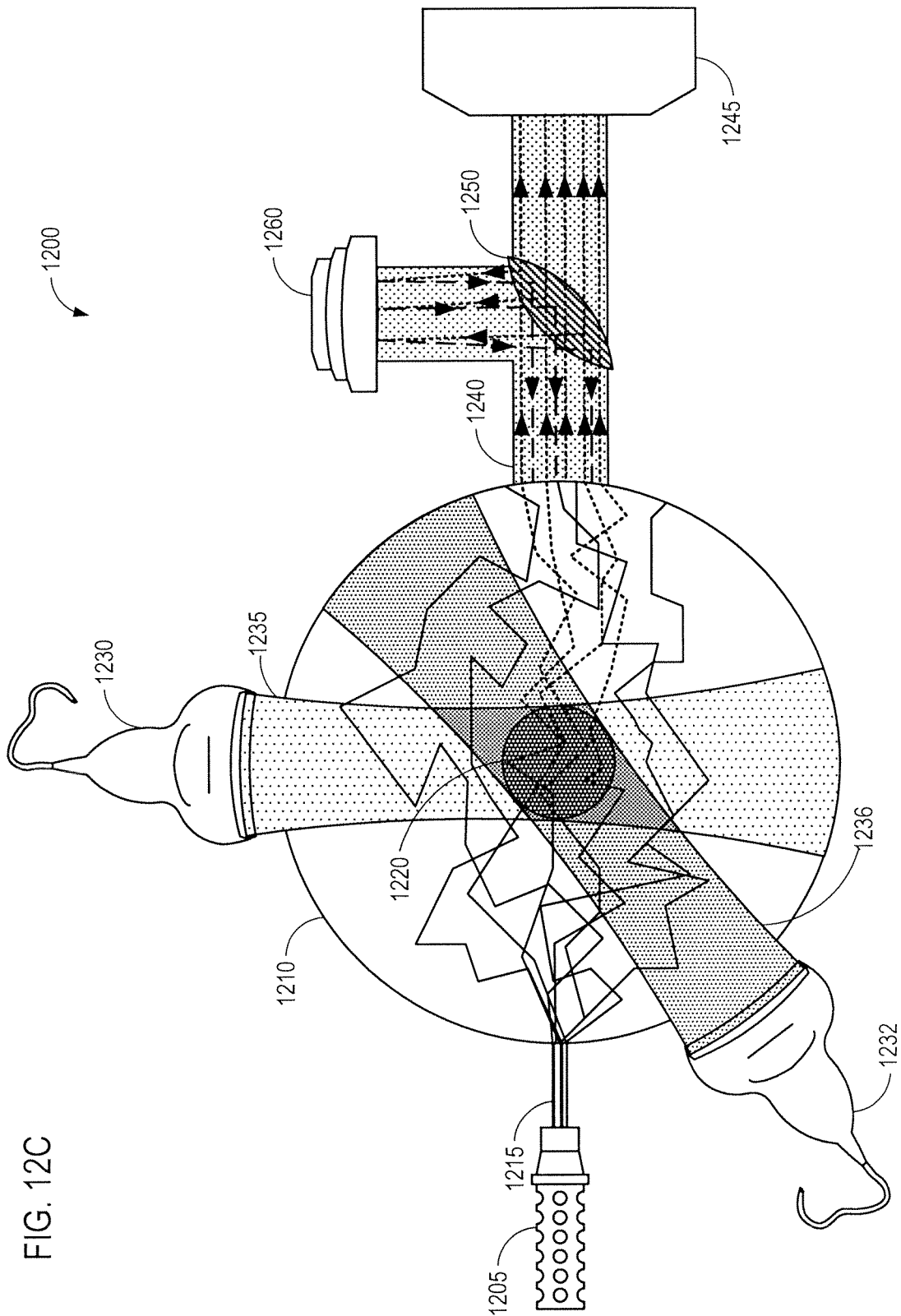
FIG. 12C illustrates EMR modulated by two focused acoustical waves reflected by a phase conjugating mirror.

FIG. 12C illustrates the system 1200 in which a beam splitter 1250 diverts at least some of the modulated EMR 1240 to a phase conjugating mirror 1260. In the illustrated embodiment, at least some of the EMR 1215 scattered from the focus volume 1220 may be modulated at a beat frequency of the first and second acoustical waves 1235 and 1236. In some embodiments, a filter may remove unmodulated EMR and EMR modulated at anything other than one or more specific functions of the frequencies of the first and second acoustical waves 1235 and 1236. EMR 1240 modulated at the one or more specific functions of the frequencies of the first and second acoustical waves 1235 and 1236 may be reflected by the phase conjugating mirror 1260.

The reflected phase conjugated EMR may retrace a turbid path back to the focus volume and again be scattered. In some embodiments, the phase conjugated EMR may retrace the turbid path back to the focus volume in order to provide an EMR therapy. In some embodiments, the phase conjugated EMR scattered by the focus volume may be used to image the focus volume.

Figure 13:
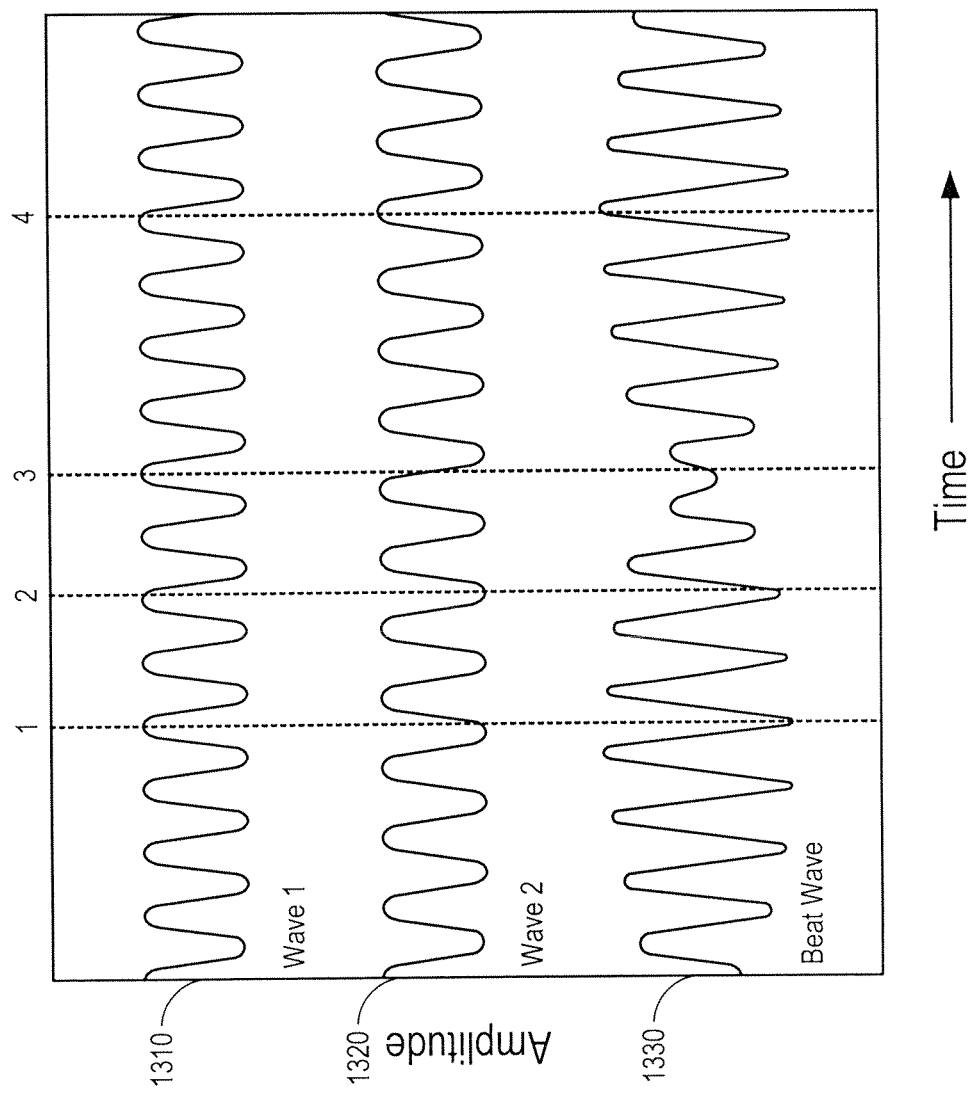
FIG. 13 illustrates a graphical representation of a beat frequency of two acoustical waves.

FIG. 13 illustrates a graphical representation 1300 of a beat frequency 1330 of two acoustical waves 1310 and 1320. In the simplified graphical representation 1300, the first wave 1310 and the second wave 1320 are out of phase, such that the local minimums and local maximums are out of sync. By adding the magnitude of the first and second waves, a beat wave 1330 can be generated. The frequency of the beat wave 1330 can be visualized with local maximums at markers 1 and 4 and a local minimum at marker 3.

Figure 14:
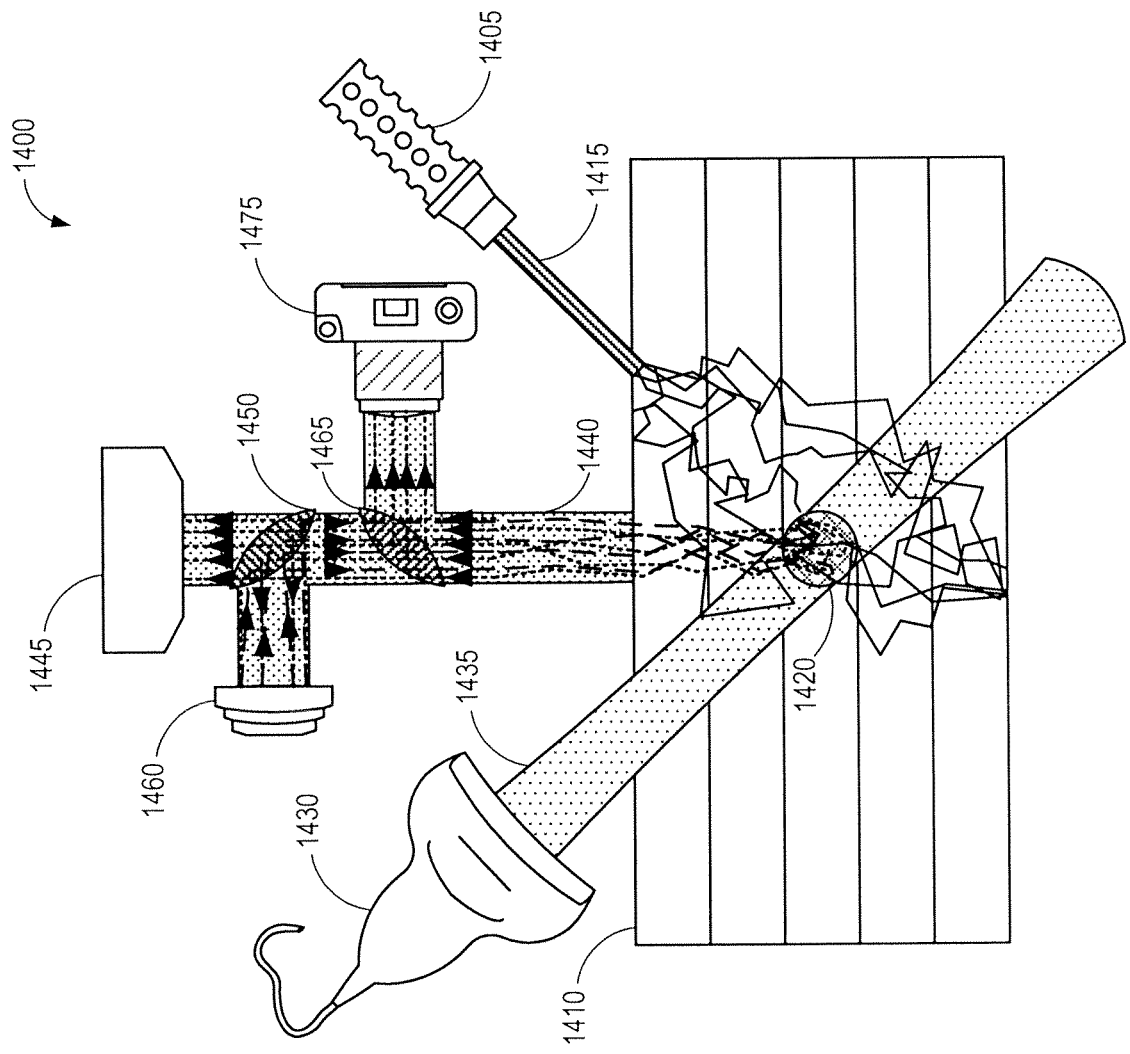
FIG. 14 illustrates EMR modulated by an acoustical wave focused on a layer of a multi-layered diffusion medium.

FIG. 14 illustrates a system 1400 in which EMR 1440 is focused on a focus region 1420, using ultrasonic modulation by an acoustical wave 1435, on a layer of a multi-layered diffusion medium 1410. As illustrated, a light source 1405, such as a laser, may irradiate the diffusion medium 1410 with an EMR 1415. The EMR 1415 may scatter within the diffusion medium 1410. Some of the EMR 1415 may scatter from the focus region 1420, such as an interface between layers or a surface of a layer of the diffusion medium 1410. The EMR 1415 scattered from the focus region 1420 may be modulated at a function of the frequency of the acoustical wave 1435.

The modulated EMR 1440 may be diverted by one or more beam splitter 1450 and 1465 to a receiver 1445, an imaging device 1475, and/or a phase conjugating mirror 1460. The phase conjugating mirror 1460 may reflect the modulated EMR 1440 in reverse through the turbid path back to the focus region 1420. The phase conjugated EMR scattered from the focus region 1420 may then be received by receiver 1445, imaging device 1475, and/or phase conjugating mirror 1460.

Figure 15:
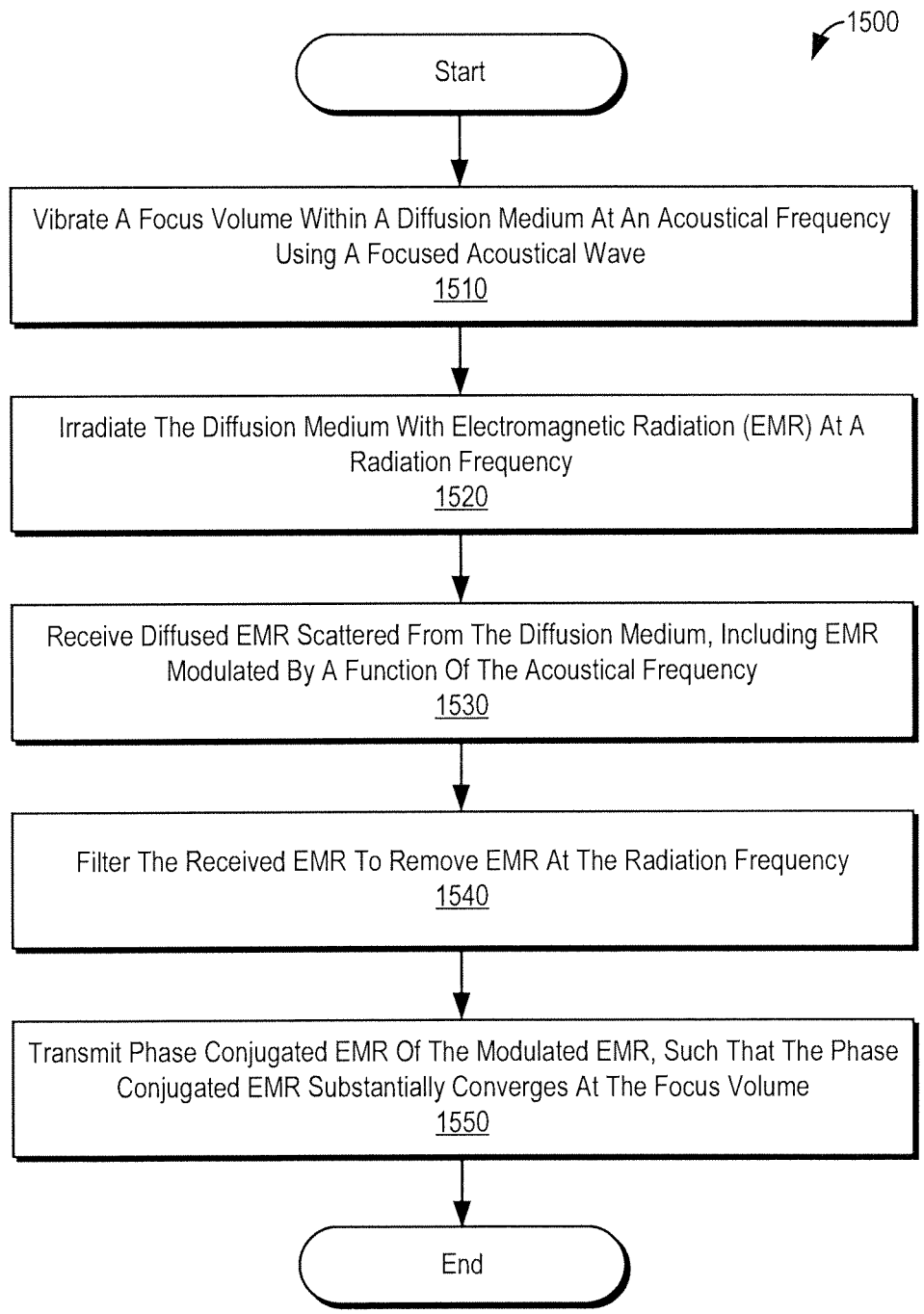
FIG. 15 illustrates a flow chart of a method for focusing EMR using phase conjugation of harmonically modulated EMR.

FIG. 15 illustrates a flow chart of a method 1500 for focusing EMR using phase conjugation of harmonically modulated EMR. Initially, a focus volume within a diffusion medium is vibrated at an acoustical frequency using a focused acoustical wave, at 1510. The diffusion medium is irradiated with EMR at a radiation frequency, at 1520. EMR, including EMR modulated by a function of the acoustical frequency of the focused acoustical wave scattered from the diffusion medium, is received, at 1530. For example, the EMR scattered from the focus volume may be modulated at a harmonic, such as the second or third harmonic, of the frequency of the acoustical wave.

A filter may remove EMR at the original radiation frequency and/or EMR modulated at a harmonic of the acoustical frequency that is not being used for detection, at 1540. Phase conjugated EMR of the harmonically modulated EMR may be transmitted, such that the harmonically modulated EMR substantially converges at the focus volume, at 1550.

Figure 16:
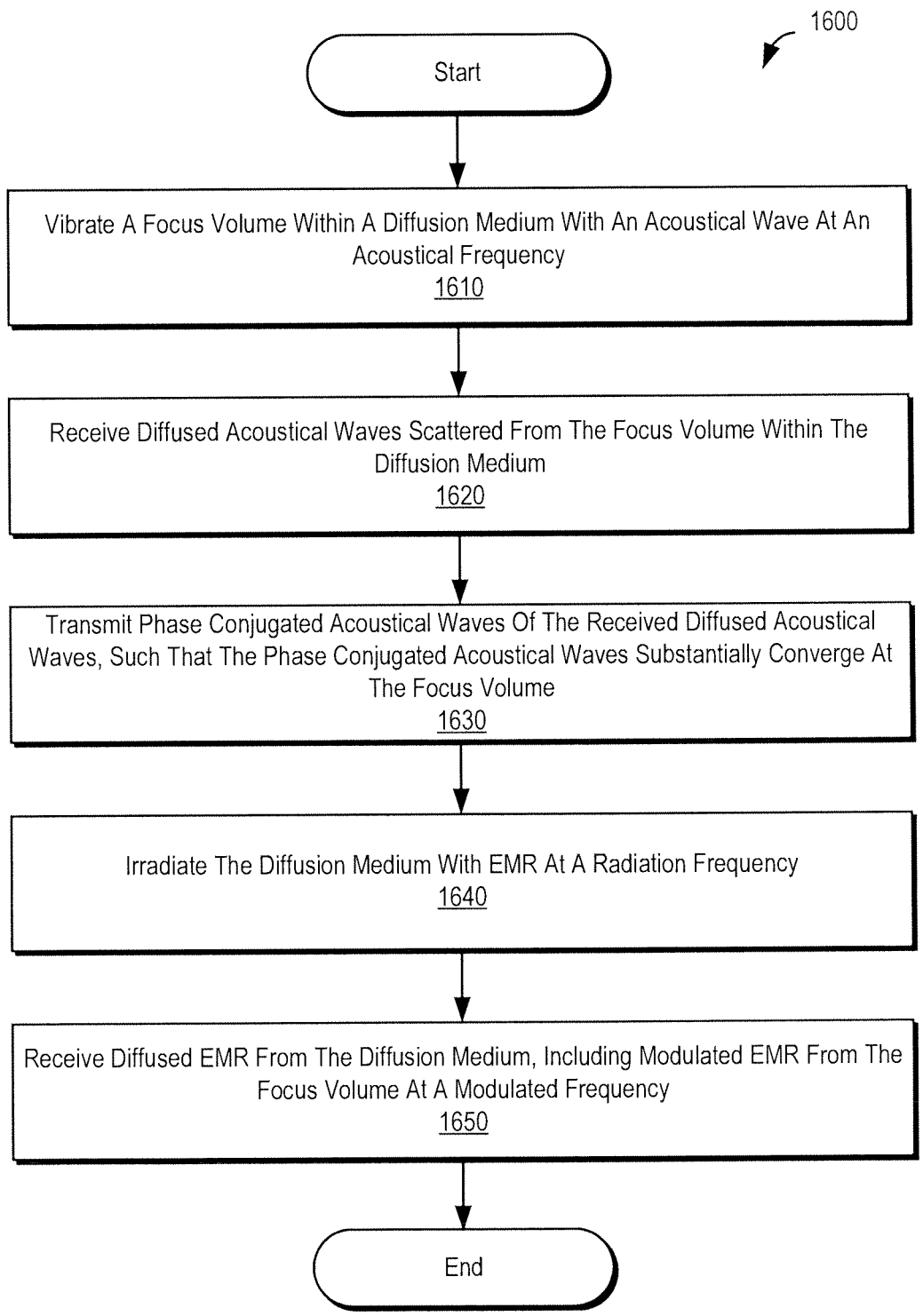
FIG. 16 illustrates a flow chart of a method for focusing an ultrasonic wave using acoustical phase conjugation.

FIG. 16 illustrates a flow chart of a method 1600 for focusing an ultrasonic wave using acoustical phase conjugation. A focus volume may be vibrated using a first acoustical wave at a first acoustical frequency, at 1610. Diffused acoustical waves, including those scattered from the focus volume, may be received, at 1620. Acoustical phase conjugation may be utilized to reflect, and potentially amplify, the acoustical waves, such that the phase conjugated acoustical waves substantially converge at the focus volume, at 1630. In such an embodiment, the focus volume may vibrate with greater intensity at the focus volume than would be possible using only a focused acoustical wave.

The diffusion medium may be irradiated with EMR at a radiation frequency, at 1640. The EMR emerging from the diffusion medium may include modulated EMR from the focus volume modulated at a function of the acoustical frequency, at 1650. In some embodiments, the received modulated EMR may be reflected using a phase conjugating mirror, and potentially amplified, in order to increase the amount of EMR scattered from the focus volume.

Figure 17:
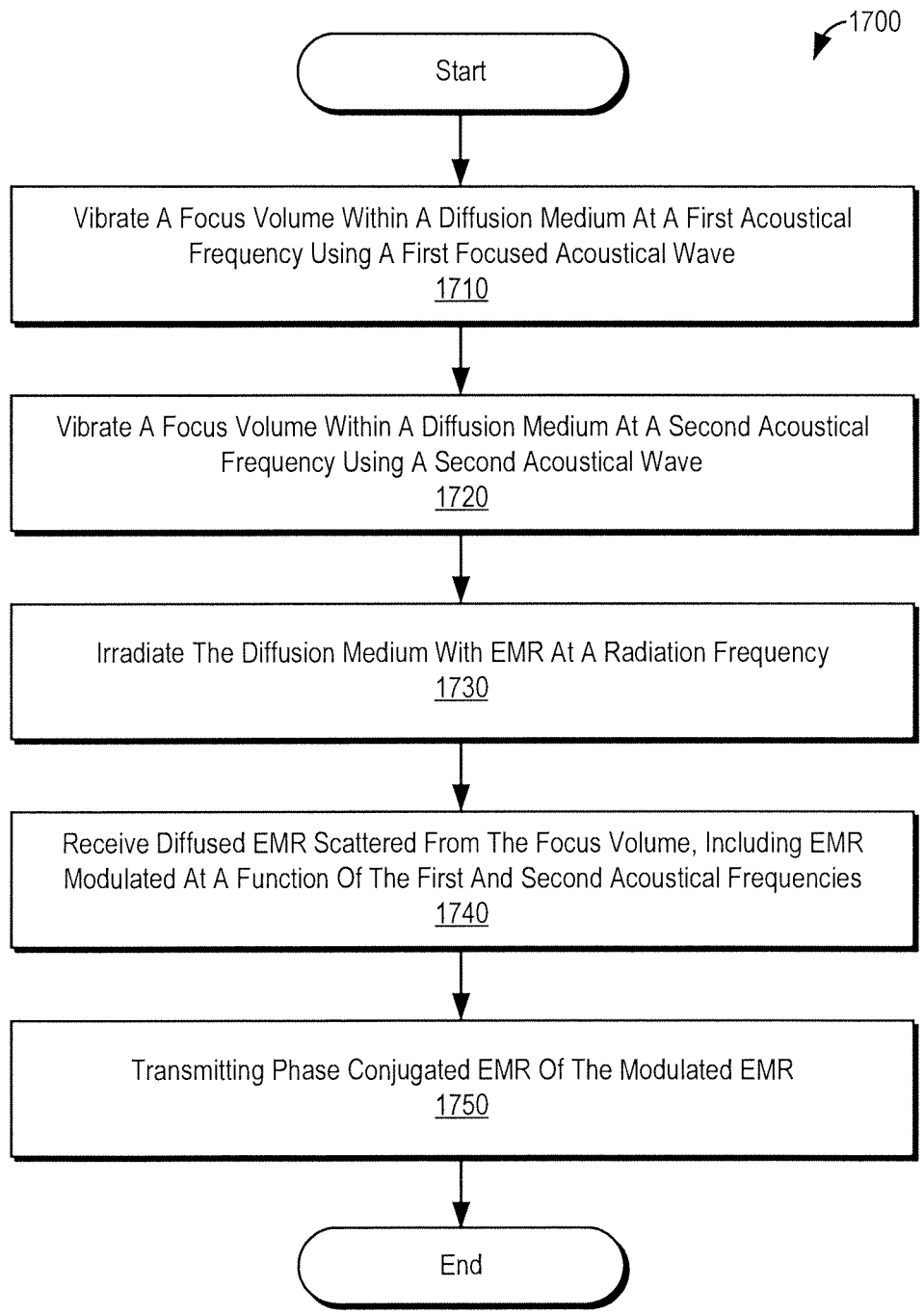
FIG. 17 illustrates a flow chart of a method for focusing EMR modulated using a plurality of acoustical waves.

FIG. 17 illustrates a flow chart of a method for focusing EMR modulated using a plurality of acoustical waves. A focus volume may be vibrated using a first acoustical wave at a first acoustical frequency, at 1710, and vibrated using a second acoustical wave at a second acoustical frequency, at 1720. The diffusion medium may be irradiated with EMR at a radiation frequency, at 1730. A receiver may receive diffused EMR scattered from the diffusion medium, including EMR scattered from the focus volume that is modulated at a function of the frequencies of the first and second acoustical frequencies, at 1740. In some embodiments, a phase conjugating mirror may be configured to reflect and/or amplify the modulated EMR, at 1750.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined by the following claims.

What is claimed is:

1. A method for focusing electromagnetic radiation using phase conjugation of harmonically modulated electromagnetic radiation, comprising:
   vibrating a focus volume within a diffusion medium at an acoustical frequency, $f_a$, using a focused acoustical wave;
   irradiating the diffusion medium with electromagnetic radiation at a radiation frequency, $f_r$;
   receiving diffused electromagnetic radiation scattered from the diffusion medium, including harmonically modulated electromagnetic radiation from the focus volume at a modulated frequency, $f_r$ shifted by a harmonic of the acoustical frequency, $Nf_a$, where N is an integer greater than 1;
   filtering received diffused electromagnetic radiation to remove electromagnetic radiation at the radiation frequency, $f_r$, and at modulated frequencies shifted by the first harmonic of the acoustical frequency, $1f_a$; and
   transmitting phase conjugated electromagnetic radiation of filtered harmonically modulated electromagnetic radiation, such that the phase conjugated electromagnetic radiation substantially converges at the focus volume.

2. The method of claim 1, further comprising:
   receiving diffused phase conjugated electromagnetic radiation scattered substantially from the focus volume;
   determining absorption rates of the phase conjugated electromagnetic radiation in hemoglobin in the focus volume at a plurality of radiation frequencies; and
   calculating a blood oxygenation within the focus volume using the determined absorption rates.

3. The method of claim 1, wherein the diffusion medium comprises a brain, and wherein the radiation frequency, $f_r$, is between 700 nanometers and 1500 nanometers, and further comprising:
   receiving diffused phase conjugated electromagnetic radiation scattered substantially from the focus volume; and
   measuring a level of neuronal activity in the brain using functional near-infrared (fNIR) imaging.

4. The method of claim 1, further comprising:
receiving diffused phase conjugated electromagnetic radiation scattered substantially from the focus volume; and
generating an image of the focus volume using the received diffused phase conjugated electromagnetic radiation from the focus volume.

5. The method of claim 1, further comprising:
receiving diffused phase conjugated electromagnetic radiation scattered substantially from the focus volume; and
determining a characteristic of a motion of a fluid within the focus volume using a Doppler measurement of the received phase conjugated electromagnetic radiation from the focus volume.

6. The method of claim 1, wherein the electromagnetic radiation has a frequency bandwidth less than the acoustical frequency, $f_a$.

7. The method of claim 1, wherein the harmonically modulated electromagnetic radiation is modulated at a second harmonic, such that the harmonically modulated electromagnetic radiation is at a modulated frequency $f_r$, shifted by the second harmonic of the acoustical frequency, $2f_a$.

8. The method of claim 1, wherein the harmonically modulated electromagnetic radiation is modulated at a third harmonic, such that the harmonically modulated electromagnetic radiation is at a modulated frequency $f_r$, shifted by the third harmonic of the acoustical frequency, $3f_a$.

9. The method of claim 1, wherein the harmonically modulated electromagnetic radiation includes electromagnetic radiation modulated at a plurality of harmonics, including electromagnetic radiation modulated at first, second, third, and fourth harmonics, such that the harmonically modulated electromagnetic radiation includes modulated frequencies $f_r$ shifted by the first harmonic of the acoustical frequency $1f_a$, $f_r$ shifted by the second harmonic of the acoustical frequency $2f_a$, $f_r$ shifted by the third harmonic of the acoustical frequency $3f_a$, and $f_r$ shifted by the fourth harmonic of the acoustical frequency $4f_a$.

10. The method of claim 9, further comprising:
receiving diffused phase conjugated electromagnetic radiation modulated at the plurality of harmonics scattered substantially from the focus volume; and
generating an image of the focus volume using the received diffused phase conjugated electromagnetic radiation from the focus volume.

11. The method of claim 1, wherein transmitting the phase conjugated electromagnetic radiation is performed in real-time using a phase conjugate mirror (PCM).

12. The method of claim 1, wherein transmitting the phase conjugated electromagnetic radiation is performed using degenerate four-wave mixing in a phase conjugate mirror (PCM).

13. The method of claim 1, wherein vibrating the focus volume comprises vibrating an elongated volume having a first end and a second end; and
wherein the acoustical frequency of the elongated volume is configured to transition from a first acoustical frequency at the first end of the elongated volume to a second acoustical frequency at the second end of the elongated volume, such that the harmonically modulated electromagnetic radiation is shifted by a distinct acoustical frequency depending on from where along the elongated volume the electromagnetic radiation was scattered.

14. The method of claim 13, further comprising using acoustical diffraction of the focused acoustical wave in order to cause the acoustical frequency of the elongated volume to transition from a first acoustical frequency at the first end of the elongated volume to a second acoustical frequency at the second end of the elongated volume.

15. The method of claim 1, further comprising:
shifting the frequency of the phase conjugated electromagnetic radiation by $Nf_a$, such that the frequency of the phase conjugated electromagnetic radiation that substantially converges at the focus volume is the radiation frequency, $f_r$.

16. A system for focusing electromagnetic radiation using phase conjugation of harmonically modulated electromagnetic radiation, comprising:
a transducer configured to generate a focused acoustical wave to vibrate a focus volume within a diffusion medium at an acoustical frequency, $f_a$;
a light source configured to irradiate the diffusion medium with electromagnetic radiation at a radiation frequency, $f_r$;
a receiver configured to receive diffused electromagnetic radiation scattered from the focus volume, including harmonically modulated electromagnetic radiation from the focus volume at a modulated frequency, $f_r$ shifted by $Nf_a$, where N is an integer greater than 1;
a filter configured to remove electromagnetic radiation at the radiation frequency, $f_r$, and at modulated frequencies shifted by the first harmonic of the acoustical frequency, $1f_a$, from the received diffused electromagnetic radiation; and
a transmitter configured to transmit phase conjugated electromagnetic radiation of the filtered harmonically modulated electromagnetic radiation, such that the phase conjugated electromagnetic radiation substantially converges at the focus volume.

17. The system of claim 16, wherein the transmitter is configured to transmit phase conjugated electromagnetic radiation of the filtered harmonically modulated electromagnetic radiation, such that the phase conjugated electromagnetic radiation substantially converges at the focus volume to activate a drug within the focus volume.

18. The system of claim 16, wherein the transmitter comprises a phase conjugate mirror configured to use a pumping beam to create an energy build up in a non linear standing wave in order to amplify the phase conjugated electromagnetic radiation relative to the amplitude of the filtered harmonically modulated electromagnetic radiation.

19. The system of claim 16, wherein the radiation frequency, $f_r$, comprises an infrared frequency.

20. The system of claim 16, wherein the light source is configured to sweep the radiation frequency, $f_r$, between an initial frequency and a final frequency.

21. The system of claim 16, further comprising:
an ultrasonic receiver configured to receive diffused acoustical waves scattered from the focus volume within the diffusion medium; and
an acoustical transmitter configured to transmit phase conjugated acoustical waves of the received diffused acoustical waves, such that the phase conjugated acoustical waves substantially converge at the focus volume.

22. The system of claim 16, further comprising:
a second transducer configured to generate a second acoustical wave within the diffusion medium, such that the acoustical frequency, $f_a$, is a function of the frequency of the focused acoustical wave and the frequency of the second acoustical wave.

23. The system of claim 22, wherein the acoustical frequency, $f_a$, is an absolute value of a difference between the frequency of the focused acoustical wave and the frequency of the second acoustical wave, such that the acoustical frequency, $f_a$, is a beat frequency of the focused acoustical wave and the second acoustical wave.

24. The system of claim 16, wherein the transducer is configured to sequentially vibrate each of a plurality of focus volumes within the diffusion medium,
- wherein the light source is configured to irradiate the sequentially vibrated plurality of focus volumes within the diffusion medium,
- wherein the receiver is configured to sequentially receive diffused electromagnetic radiation scattered from the diffusion medium, including harmonically modulated electromagnetic radiation from each of the sequentially vibrated focus volumes at the modulated frequency, $f_r$, shifted by $Nf_a$,
- wherein the filter is configured to sequentially remove electromagnetic radiation at the radiation frequency, $f_r$, and at modulated frequencies shifted by the first harmonic of the acoustical frequency, $1f_a$, from the received diffused electromagnetic radiation,
- wherein the transmitter is configured to sequentially transmit phase conjugated electromagnetic radiation of the sequentially filtered harmonically modulated electromagnetic radiation, such that the phase conjugated electromagnetic radiation substantially converges at each of the plurality of focus volumes, sequentially,
- wherein the receiver is further configured to sequentially receive diffused phase conjugated electromagnetic radiation scattered substantially from each of the plurality of focus volumes, including harmonically modulated electromagnetic radiation from each of the sequentially vibrated focus volumes at the modulated frequency, $f_r$, shifted by $Nf_a$,
- wherein the system further comprises an imaging device configured to sequentially generate an image of each of the focus volumes using the received diffused phase conjugated electromagnetic radiation from each of the focus volumes, and
- wherein the system further comprises an image merger module configured to merge the images of each of the plurality of focus volumes to form an image of the diffusion medium.

25. A method for focusing an ultrasonic wave in an acousto-optical radiation system using acoustical phase conjugation, comprising:
- vibrating a focus volume within a diffusion medium at an acoustical frequency, $f_a$, using an acoustical wave;
- receiving diffused acoustical waves scattered from the focus volume within the diffusion medium;
- transmitting phase conjugated acoustical waves of the received diffused acoustical waves, such that the phase conjugated acoustical waves substantially converge at the focus volume;
- irradiating the diffusion medium with electromagnetic radiation at a radiation frequency, $f_r$; and
- receiving diffused electromagnetic radiation from the diffusion medium, including modulated electromagnetic radiation from the focus volume at a modulated frequency $f_r$ shifted by $f_a$;
- wherein the modulated electromagnetic radiation comprises harmonically modulated electromagnetic radiation modulated at a harmonic of a fundamental frequency of the electromagnetic radiation, such that the harmonically modulated electromagnetic radiation is at a modulated frequency $f_r$ shifted by a harmonic of the acoustical frequency, $Nf_a$, where N is an integer.

26. The method of claim 25, further comprising:
- determining absorption rates of the modulated electromagnetic radiation in hemoglobin in the focus volume at a plurality of radiation frequencies; and
- calculating a blood oxygenation within the focus volume using the determined absorption rates.

27. The method of claim 25, further comprising:
- transmitting phase conjugated electromagnetic radiation of the filtered modulated electromagnetic radiation, such that the phase conjugated electromagnetic radiation substantially converges at the focus volume.

28. The method of claim 27, further comprising:
- receiving diffused phase conjugated electromagnetic radiation scattered substantially from the focus volume;
- determining absorption rates of the phase conjugated electromagnetic radiation in hemoglobin in the focus volume at a plurality of radiation frequencies; and
- calculating a blood oxygenation of within the focus volume using the determined absorption rates.

29. The method of claim 27, wherein transmitting the phase conjugated electromagnetic radiation is performed using degenerate four-wave mixing in a phase conjugate mirror (PCM).

30. The method of claim 27, further comprising:
- shifting the frequency of the phase conjugated electromagnetic radiation by $f_a$, such that the frequency of the phase conjugated electromagnetic radiation that substantially converges at the focus volume is the radiation frequency, $f_r$.

31. The method of claim 27, further comprising:
- shifting the frequency of the phase conjugated electromagnetic radiation by a calibration frequency, $f_c$, such that the frequency of the phase conjugated electromagnetic radiation is useful for electromagnetic radiation therapy.

32. The method of claim 25, wherein the acoustical frequency, $f_a$, is generated using the acoustical wave and a second acoustical wave, such that the acoustical frequency, $f_a$, is a function of the frequency of the acoustical wave and the frequency of the second acoustical wave.

33. The method of claim 32, wherein the second acoustical wave is focused.

34. The method of claim 32, wherein the acoustical frequency, $f_a$, is an absolute value of a difference between the frequency of the acoustical wave and the frequency of the second acoustical wave, such that the acoustical frequency, $f_a$, is a beat frequency of the acoustical wave and the second acoustical wave.

35. A system for focusing an ultrasonic wave in an acousto-optical radiation system using acoustical phase conjugation, comprising:
- a transducer configured to generate an acoustical wave to vibrate a focus volume within a diffusion medium at an acoustical frequency, $f_a$;
- an ultrasonic receiver configured to receive diffused acoustical waves scattered from the focus volume within the diffusion medium;
- an acoustical transmitter configured to transmit phase conjugated acoustical waves of received diffused acoustical waves, such that the phase conjugated acoustical waves substantially converge at the focus volume;
- a light source configured to irradiate the diffusion medium with electromagnetic radiation at a radiation frequency, $f_r$; and
- a receiver configured to receive diffused electromagnetic radiation scattered from the focus volume, including modulated electromagnetic radiation from the focus volume at a modulated frequency, $f_r$ shifted by the acoustical frequency, $f_a$, wherein the modulated electromagnetic radiation comprises harmonically modulated electromagnetic radiation modulated at a harmonic of a fundamental frequency of the electromagnetic radiation, such that the harmonically modulated electromagnetic radiation is at a modulated frequency $f_r$ shifted by a harmonic of the acoustical frequency, $Nf_a$, where N is an integer.

36. The system of claim 35, further comprising a filter configured to remove electromagnetic radiation at the radiation frequency, $f_r$.

37. The system of claim 35, wherein the diffusion medium comprises a brain, wherein the radiation frequency, $f_r$, is between 700 nanometers and 1500 nanometers, and wherein the system further comprises a neuronal activity module configured to measure a level of neuronal activity in the brain using functional near-infrared (fNIR) imaging.

38. The system of claim 35, further comprising an imaging device configured to generate an image of the focus volume using the received diffused phase conjugated electromagnetic radiation from the focus volume.

39. The system of claim 35, wherein the modulated electromagnetic radiation is modulated at a second harmonic, such that the harmonically modulated electromagnetic radiation is at a modulated frequency $f_r$ shifted by the second harmonic of the acoustical frequency, $2f_a$.

40. The system of claim 35, wherein the modulated electromagnetic radiation includes electromagnetic radiation modulated at a plurality of harmonics, including electromagnetic radiation modulated at first, second, third, and fourth harmonics, such that the harmonically modulated electromagnetic radiation includes modulated frequencies $f_r$ shifted by the first harmonic of the acoustical frequency $1f_a$, $f_r$ shifted by the second harmonic of the acoustical frequency $2f_a$, $f_r$ shifted by the third harmonic of the acoustical frequency $3f_a$, and $f_r$ shifted by the fourth harmonic of the acoustical frequency $4f_a$.

41. The system of claim 40, further comprising an imaging device configured to generate an image of the focus volume using filtered harmonically modulated electromagnetic radiation from the focus volume.

42. The system of claim 35, wherein the focus volume comprises an elongated focus volume having a first end and a second end, wherein the transducer is configured to vibrate the elongated volume, and wherein the acoustical frequency of the elongated volume is configured to transition from a first acoustical frequency at the first end of the elongated volume to a second acoustical frequency at the second end of the elongated volume, such that the harmonically modulated electromagnetic radiation is configured to be shifted by a distinct acoustical frequency depending on from where along the elongated volume the electromagnetic radiation was scattered.

43. The system of claim 42, further comprising an acoustical diffraction system configured to diffract the acoustical wave such that the acoustical frequency of the elongated volume transitions from a first acoustical frequency at the first end of the elongated volume to a second acoustical frequency at the second end of the elongated volume.

* * * * *